Figure 1:
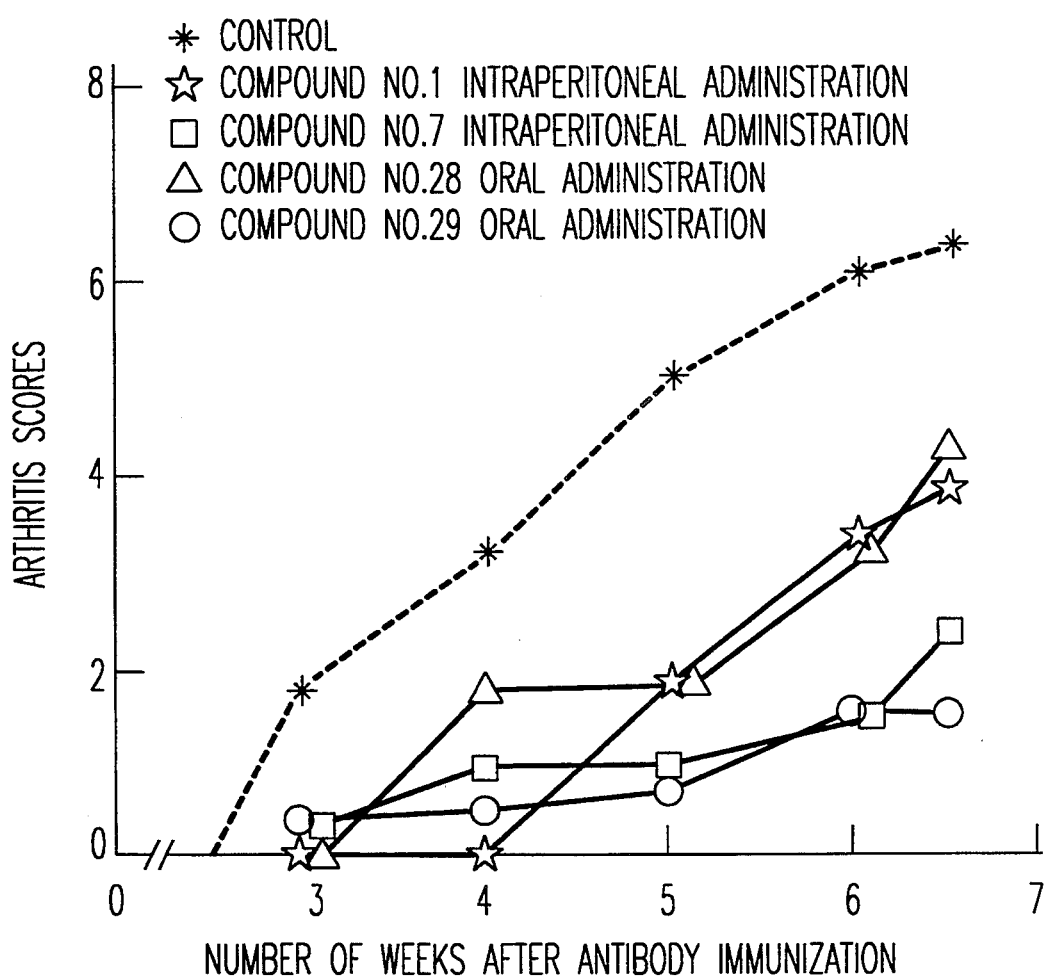

United States Patent [19]

Mizukoshi et al.

[11] Patent Number: 5,380,834
[45] Date of Patent: Jan. 10, 1995

[54] IMMUNO-SUPPRESSIVE AGENT

[75] Inventors: Sadanori Mizukoshi; Fuminori Kato; Masamitsu Tsukamoto; Kenji Kon, all of Kusatsu, Japan

[73] Assignee: Ishihara Sangyo Kaisha Ltd., Osaka, Japan

[21] Appl. No.: 11,463

[22] Filed: Jan. 27, 1993

[30] Foreign Application Priority Data

Feb. 6, 1992 [JP] Japan .................. 4-066582
Dec. 16, 1992 [JP] Japan .................. 4-361752

[51] Int. Cl.⁶ .......................... C07D 309/32
[52] U.S. Cl. .................................. 536/4.1
[58] Field of Search ............ 536/4.1; 514/25, 885

[56] References Cited

U.S. PATENT DOCUMENTS 4,256,646 3/1981 Hernandez et al. ............ 549/420

FOREIGN PATENT DOCUMENTS 4316593 11/1992 Japan .

OTHER PUBLICATIONS

Carbohydrate Research, 60 (1978) pp. C11–12, John S. Brimacombe, et al., "The Stereochemistry of the Reduciton of 1, 6–Anhydro-3, 4–Dideoxy . . . ".

Carbohydrate Research, 114 (1983), pp. 71–82, Fred Shafizadeh, et al., "Additional Reactions of Levoglucosenone."

(List continued on next page.)

Primary Examiner—Ronald W. Griffin
Attorney, Agent, or Firm—Oblon, Spivak, McClelland, Maier & Neustadt

[57] ABSTRACT

An immuno-suppressive agent containing, as an effective component, an, enopyranose derivative of the following formula (I) or its salt:

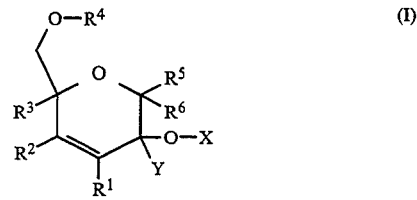

wherein $R^1$ is a hydrogen atom, alkyl which may be substituted, alkenyl, alkynyl, $-OSO_2R^7$, a halogen atom, $-OCOR^7$, $-NHCOR^8$, alkoxy, phenyl which may be substituted or a saccharose residue, $R^2$ is a hydrogen atom or alkyl, $R^3$ is a hydrogen atom or a halogen atom, $R^4$ is a hydrogen atom, $-COR^9$, silyl which may be substituted or alkyl which may be substituted, one of $R^5$ and $R^6$ is hydroxyl, alkoxy which may be substituted, a saccharose residue, cycloalkyloxy which may be substituted or $-OCOR^{10}$ and the other is a hydrogen atom or alkyl which may be substituted, or $R^4$ and $R^5$ together form a single bond, while $R^6$ is a hydrogen atom or alkyl which may be substituted, each of $R^7$, $R^9$ and $R^{10}$ is alkyl or phenyl which may be substituted, $R^8$ is alkyl, phenyl which may be substituted or benzyloxy, X is a hydrogen atom, alkyl which may be substituted, alkenyl which may be substituted, alkynyl which may be substituted, cycloalkyl which may be substituted, phenyl which may be substituted, pyridyl which may be substituted, furanyl which may be substituted, thienyl which may be substituted, formyl, $-COR^{11}$, $-C(W^1)W^2R^{11}$ or $-SO_2R^{11}$, $R^{11}$ is a chain hydrocarbon group which may be substituted, a monocyclic hydrocarbon group which may be substituted, a polycyclic hydrocarbon group which may be substituted, a monocyclic heterocycle group which may be substituted, or a polycyclic heterocycle group which may be substituted, $W^1$ is an oxygen atom or a sulfur atom, $W^2$ is an oxygen atom, a sulfur atom or $-NH-$, Y is a hydrogen atom, alkyl which may be substituted, alkenyl which may be substituted or alkynyl which may be substituted.

10 Claims, 1 Drawing Sheet

OTHER PUBLICATIONS

Carbohydrate Research, 199 (1990), pp. 243–247, Yvonne Gelas-Mialhe, et al., "New Branched-Chain and Aminodeoxys Sugars From . . . "

Carbohydrate Research, 71 (1979), pp. 169–191, Fred Shafizadeh, et al., "Some Reactions to Levoglucosenone."

Helvetica Chimica Acta, vol. 56, Fasc. 5 (1973)—Nr. 180, pp. 1792–1799, "Versuche Zur Synthese Der . . . "

Chem. Ber. 110, (1977), pp. 1994–2004, P. Koll, et al., "Neue Derivate Der 2, 7-Anhydro . . . "

Rad Jugosl.akad.znan.i umjet., Kem. 2, (1983) pp. 133–141, Dusan Miljkovic, et al., "Conformation–Reactivity Relationship in 1,6-Anhydro . . . "

Chemical Abstracts, vol. 71, No. 23, Dec. 8, 1969, p. 421, An-113208h.

Chemical Abstracts, vol. 75, No. 11, Sep. 13, 1971, p. 501, AN-77215e.

Chemical Abstracts, vol. 76, No. 13, Mar. 27, 1972, p. 403, AN-72723e.

Chemical Abstracts, vol. 76, No. 17, Apr. 24, 1972, p. 482, AN-99948u.

Chemical Abstracts, vol. 78, No. 5, Feb. 5, 1973, p. 539, AN-30143b.

Chemical Abstracts, vol. 78, No. 5, Feb. 5, 1973, p. 539, AN-30144c.

Chemical Abstracts, vol. 78, No. 11, Mar. 19, 1973, p. 508, AN-72487x.

Chemical Abstracts, vol. 78, No. 13, Apr. 2, 1973, p. 462, AN-84659t.

Chemical Abstracts, vol. 78, No. 25, Jun. 25, 1973, p. 455, AN-160054j.

Chemical Abstracts, vol. 80, No. 7, Feb. 18, 1974, p. 326, AN-37400h.

Chemical Abstracts, vol. 80, No. 23, Jun. 10, 1974, p. 507, AN 133710e.

Chemical Abstracts, vol. 81, No. 17, Oct. 28, 1974, p. 565, AN-105830w.

Chemical Abstracts, vol. 82, No. 23, Jun. 9, 1975, p. 646, AN-156638t.

Chemical Abstracts, vol. 83, No. 11, Sep. 15, 1975, p. 637, AN-97757b.

Chemical Abstracts, vol. 83, No. 19, Nov. 19, 1975, p. 580, An-164449t.

Chemical Abstracts, vol. 83, No. 23, Dec. 8, 1975, p. 499, AN-193604v.

Chemical Abstracts, vol. 84, No. 19, May 10, 1976, p. 537, AN-135994g.

Chemical Abstracts, vol. 84, No. 23, Jun. 7, 1976, p. 503, AN-165150w.

Chemical Abstracts, vol. 86, No. 11, Mar. 14, 1977, p. 653, AN-73024w.

Chemical Abstracts, vol. 87, No. 25, Dec. 19, 1977, p. 670, AN-200858u.

Chemical Abstracts, vol. 88, No. 9, Feb. 27, 1978, p. 405, AN 62540b.

Chemical Abstracts, vol. 88, No. 25, Jun. 19, 1978, p. 736, AN-190528r.

Chemical Abstracts, vol. 90, No. 5, Jan. 29, 1979, p. 513, AN-39142f.

Chemical Abstracts, vol. 90, No. 16, Apr. 16, 1979, p. 640, AN-131093p.

Chemical Abstracts, vol. 90, No. 17, Apr. 23, 1979, AN-138118.

Chemical Abstracts, vol. 92, No. 9, Mar. 3, 1980, p. 718, AN-76872f.

Chemical Abstracts, vol. 93, No. 13, Sep. 29, 1980, p. 692, AN-132748e.

Chemical Abstracts, vol. 93, No. 21, Nov. 24, 1980, p. 721, AN-204964x.

Chemical Abstracts, vol. 94, No. 17, Apr. 27, 1981, p. 792, AN-140064q.

Chemical Abstracts, vol. 95, No. 3, Jul. 20, 1981, p. 735, AN-25408p.

Chemical Abstracts, vol. 96, No. 7, Feb. 15, 1982, p. 650, AN-52606d.

Chemical Abstracts, vol. 96, No. 13, Mar. 29, 1982, p. 675, AN-103915p.

Chemical Abstracts, vol. 96, No. 23, Jun. 7, 1982, p. 711, AN-200057t.

Chemical Abstracts, vol. 97, No. 5, Aug. 2, 1982, p. 607, AN-39251k.

Chemical Abstracts, vol. 97, No. 17, Oct. 25, 1982, p. 724, AN-145197g.

Chemical Abstracts, vol. 102, No. 9, Mar. 4, 1985, p. 636, AN-79260r.

(List continued on next page.)

OTHER PUBLICATIONS

Chemical Abstracts, vol. 102, No. 13, Apr. 1, 1985, p. 677, AN-113128r.
Chemical Abstracts, vol. 103, No. 23, Dec. 9, 1985, p. 705, AN-196330v.
Chemical Abstracts, vol. 105, No. 13, Sep. 29, 1986, p. 708, AN-115324n.
Chemical Abstracts, vol. 107, No. 5, Aug. 3, 1987, p. 736, AN-40142g.
Chemical Abstracts, vol. 107, No. 11, Sep. 14, 1987, p. 718, AN-96980w.
Chemical Abstracts, vol. 107, No. 19, Nov. 9, 1987, p. 693, AN-175734x.
Chemical Abstracts, vol. 108, No. 7, Feb. 15, 1988, p. 763, AN-56455t.
Chemical Abstracts, vol. 108, No. 15, Apr. 11, 1988, p. 795, AN-132188a.
Chemical Abstracts, vol. 108, No. 19, May 9, 1988, p. 687, AN-167814d.
Chemical Abstracts, vol. 109, No. 7, Aug. 15, 1988, p. 662, AN-54555x.
Chemical Abstracts, vol. 109, No. 21, Nov. 21, 1988, p. 746, AN-190680m.
Chemical Abstracts, vol. 110, No. 5, Jan. 30, 1989, p. 574, AN-39256c.
Chemical Abstracts, vol. 110, No. 23, Jun. 5, 1989, p. 787, AN-213189v.
Chemical Abstracts, vol. 111, No. 7, Aug. 14, 1989, p. 803, AN-58188u.
Chemical Abstracts, vol. 112, No. 19, May 7, 1990, p. 728, AN-178563e.
Chemical Abstracts, vol. 113, No. 13, Sep. 24, 1990, p. 734, AN-115700x.
Chemical Abstracts, vol. 115, No. 7, Aug. 19, 1991, p. 845.
Chemical Abstracts, vol. 86, No. 21, May 23, 1977, p. 498, AN-155908b.
Chemical Abstracts, vol. 91, No. 17, Oct. 22, 1979, p. 619, AN-140416u.
Chemical Abstracts, vol. 93, No. 4, Aug. 4, 1980, p. 871, AN-46059x.

IMMUNO-SUPPRESSIVE AGENT

The present invention relates to an immuno-suppressive agent containing an enopyranose derivative of the formula (I) as an effective component.

An immuno-suppressive agent is usually used for treating a disease caused by abnormal sthenia of an immunological function, for example, a so-called autoimmune disease such as rheumatoid arthritis, systemic lupus erythematosus, chronic nephritis, chronic thyroiditis or autoimmune hemolytic anemia or for suppressing a rejection at the time of transplantation of an organ. Heretofore, steroid hormone, azathioprine and cyclophosphamide have been used as immuno-suppressive agents.

However, conventional immuno-suppressive agents are active not only against lymphocytes but also against a wide range of cells non-selectively to give influences over their functions and proliferation. Thus, serious side effects such as agranulocytosis and renal injury have been problematic.

Thus, it has been desired to develop a drug which has a strong activity to control an immunological function and which has no substantial side effect.

The present inventors have found that an enopyranose derivative having a chemical structure totally different from conventional immuno-suppressive agents, has immuno-suppressive activities. The present invention has been accomplished on the basis of this discovery.

Thus, the present invention provides an immuno-suppressive agent or an anti-inflammatory agent containing, as an effective component, an enopyranose derivative of the following formula (I) or its salt:

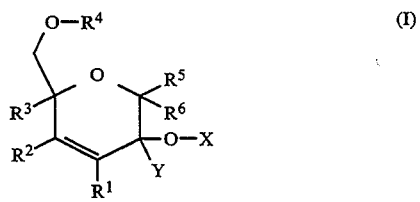

wherein $R^1$ is a hydrogen atom, alkyl which may be substituted, alkenyl, alkynyl, $-OSO_2R^7$, a halogen atom, $-OCOR^7$, $-NHCOR^8$, alkoxy, phenyl which may be substituted or a saccharose residue, $R^2$ is a hydrogen atom or alkyl, $R^3$ is a hydrogen atom or a halogen atom, $R^4$ is a hydrogen atom, $-COR^9$, silyl which may be substituted or alkyl which may be substituted, one of $R^5$ and $R^6$ is hydroxyl, alkoxy which may be substituted, a saccharose residue, cycloalkyloxy which may be substituted or $-OCOR^{10}$ and the other is a hydrogen atom or alkyl which may be substituted, or $R^4$ and $R^5$ together form a single bond, while $R^6$ is a hydrogen atom or alkyl which may be substituted, each of $R^7$, $R^9$ and $R^{10}$ is alkyl or phenyl which may be substituted, $R^8$ is alkyl phenyl which may be substituted or benzyloxy, X is a hydrogen atom, alkyl which may be substituted, alkenyl which may be substituted, alkynyl which may be substituted, cycloalkyl which may be substituted, phenyl which may be substituted, pyridyl which may be substituted, furanyl which may be substituted, thienyl which may be substituted, formyl, $-COR^{11}$, $-C(W^1)W^2R^{11}$ or $-SO_2R^{11}$, $R^{11}$ is a chain hydrocarbon group which may be substituted, a monocyclic hydrocarbon group which may be substituted, a polycyclic hydrocarbon group which may be substituted, a monocyclic heterocycle group which may be substituted, or a polycyclic heterocycle group which may be substituted, $W^1$ is an oxygen atom or a sulfur atom, $W^2$ is an oxygen atom, a sulfur atom or $-NH-$, Y is a hydrogen atom, alkyl which may be substituted, alkenyl which may be substituted or alkynyl which may be substituted.

Now, the present invention will be described in detail with reference to the preferred embodiments.

In the accompanying drawing, FIG. 1 is a graph showing the inhibiting effects of the compounds of the formula (I) on collagen-induced arthritis model.

The alkyl group represented by or the alkyl moiety of a functional group represented by each of $R^1$, $R^2$, $R^4$, $R^5$, $R^6$, $R^7$, $R^8$, $R^9$, $R^{10}$, X and Y in the formula (I), may be $C_1$-$C_{20}$ alkyl such as methyl, ethyl, propyl, butyl, pentyl, hexyl, hepthyl, octyl, nonyl, decyl, tetradecyl, pentadecyl, octadecyl or nonadecyl, and they include linear or branched aliphatic structural isomers. The alkenyl group represented by each of $R^1$, X and Y may be $C_2$-$C_{20}$ alkenyl such as ethenyl, propenyl or butenyl, and they include linear or branched aliphatic structural isomers. The alkynyl group represented by each of $R^1$, X and Y, may be $C_2$-$C_{20}$ alkynyl such as ethynyl, propynyl or butynyl, and they also include linear or branched aliphatic structural isomers.

The halogen atom represented by each of $R^1$ and $R^3$ in the formula (I) may be a fluorine atom, a chlorine atom, a bromine atom or an iodine atom.

The saccharose residue represented by each of $R^1$, $R^5$ and $R^6$ in the formula (I) may, for example, be:

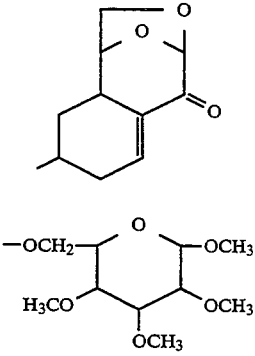

The cycloalkyl group represented by or the cycloalkyl moiety of a cycloalkyloxy group represented by each of $R^5$, $R^6$ and X in the formula (I), may be $C_3$-$C_8$ cycloalkyl such as cyclopropyl, cyclobutyl, cyclopentyl, cyclohexyl, cycloheptyl or cyclooctyl.

The substituent for the phenyl which may be substituted, represented by each of $R^1$, $R^7$, $R^8$, $R^9$ and $R^{10}$ in the formula (I), may be a halogen atom such as fluorine, chlorine, bromine or iodine, alkyl such as methyl or ethyl, or nitro.

The substituent for the silyl which may be substituted, represented by $R^4$ in the formula (I), may be alkyl such as methyl, ethyl, propyl or butyl, or phenyl.

The substituent for the alkyl which may be substituted, the alkoxy which may be substituted, or the cycloalkyloxy which may be substituted, represented by each of $R^1$, $R^4$, $R^5$ and $R^6$ in the formula (I), may be alkoxy such as methoxy or ethoxy, phenyl or hydroxyl.

The number of such substituents may be one or more. If the number is two or more, such a plurality of substituents may be the same or different.

Further, in the definitions of X and Y in the formula (I), the substituent for the alkyl which may be substituted, the alkenyl which may be substituted or the alkynyl which may be substituted, may be a halogen atom such as fluorine, chlorine, bromine or iodine, hydroxyl, phenyl, alkyl-substituted phenyl such as tolyl or xylyl, pyridyl, furanyl, thienyl, acyloxy such as acetoxy or varelyloxy, azide, or amino. Further, in the definition of X, the substituent for the cycloalkyl which may be substituted, the phenyl which may be substituted, the pyridyl which may be substituted, the furanyl which may be substituted or the thienyl which may be substituted, may be a halogen atom such as a fluorine, chlorine, bromine or iodine, hydroxyl, alkyl such as methyl or ethyl, acyloxy such as acetoxy or varelyloxy, nitro, or amino. The number of such substituents may be one or more. When the number is two or more, such a plurality of substituents may be the same or different.

In the formula (I), the chain hydrocarbon group for $R^{11}$ may be alkyl, alkenyl or alkynyl. The monocyclic hydrocarbon group may be cycloalkyl, cycloalkenyl or phenyl. The polycyclic hydrocarbon group may be a condensed polycyclic hydrocarbon group such as naphthyl, tetrahydronaphthyl or indanyl, or a bridged polycyclic hydrocarbon group such as adamantyl, noradamantyl, norbornanyl or norbornanonyl. The monocyclic heterocycle group may be pyrrolyl, furanyl, thienyl, pyrazolyl, imidazolyl, oxazolyl, isoxazolyl, thiazolyl, isothiazolyl, thiadiazolyl, pyrrolinyl, pyrrolidinyl, dihydrofuranyl, tetrahydrofuranyl, dihydrothienyl, tetrahydrothienyl, pyrazolinyl, hydantoinyl, oxazolinyl, isoxazolinyl, isoxazolidinyl, thiazolinyl, thioazolidinyl, dioxolanyl, dithiolanyl, pyridyl, pyridazinyl, pyrimidinyl, pyrazinyl, dihydropyridyl, tetrahydropyridyl, piperidinyl, dihydrooxopyridazinyl, tetrahydrooxapyridazinyl, dihydrooxopyrimidinyl, tetrahydrooxopyrimidinyl, piperazinyl, dihydropyranyl, tetrahydropyranyl, dioxanyl, dihydrodithinyl, dithianyl or morphorinyl. The polycyclic heterocycle group may be a condensed polycyclic heterocycle group such as thienothienyl, dihydrocyclopentathienyl, indolyl, benzofuranyl, benzothienyl, benzoxazolyl, benzisoxazolyl, benzothiazolyl, benzimidazolyl, tetrahydrobenzothienyl, dihydrobenzofuranyl, tetrahydrobenzisoxazolyl, benzodioxolyl, quinolinyl, isoquinolinyl, benzodioxanyl or quinoxalinyl, or a bridged polycyclic heterocycle group such as quinuclidinyl.

The substituent for the chain hydrocarbon group which may be substituted for $R^{11}$, may be a halogen atom, alkoxy, haloalkoxy, alkylthio, cycloalkyl, cycloalkoxy, cycloalkenyl, cycloalkenyloxy, alkoxycarbonyl, carboxyl, alkylcarbonyl, alkylcarbonyloxy, aryl, aryloxy, arylthio, amino, alkyl-substituted amino. The number of such substitutents or substituents on such substitutents may be one or more. When the number is two or more, such a plurality of substituents may be the same or different.

Further, the substituent for the monocyclic hydrocarbon group which may be substituted, the polycyclic hydrocarbon group which may be substituted, the monocyclic heterocycle group which may be substituted, or the polycyclic heterocycle group which may be substituted for $R^{11}$, may be a halogen atom, alkyl, haloalkyl, alkoxy, haloalkoxy, alkylthio, cycloalkyl, cycloalkoxy, cycloalkenyl, cycloalkenyloxy, alkoxycarbonyl, alkylcarbonyl, alkylcarbonyloxy, aryl, aryloxy, arylthio, amino, alkyl-substituted amino, cyano, nitro or hydroxyl. The number of such substituents or substituents on such substituents may be one or more. When the number is two or more, such a plurality of substituents may be the same or different.

In the formula (I), the alkyl group or the alkyl moiety contained in $R^{11}$, may be $C_1$–$C_{18}$ alkyl such as methyl, ethyl, propyl, butyl, pentyl, hexyl, heptyl, octyl, decyl or nonadecyl, and they include linear or branched aliphatic structural isomers. The alkenyl contained in $R^{11}$, may be $C_2$–$C_{18}$ alkenyl such as vinyl, propenyl, butenyl, pentenyl, -hexenyl, decenyl or nonadecenyl, and they include linear or branched aliphatic structural isomers. The alkynyl group contained in $R^{11}$, may be $C_2$–$C_{18}$ alkynyl such as ethynyl, propynyl, butynyl, pentynyl, hexynyl, decynyl or nonadecynyl, and they include linear or branched aliphatic structural isomers. The cycloalkyl group or the cycloalkyl moiety contained in $R^{11}$, may be $C_3$–$C_8$ cycloalkyl such as cyclopropyl, cyclobutyl, cyclopentyl, cyclohexyl or cyclooctyl. The cycloalkenyl or the cycloalkenyl moiety contained in $R^{11}$, may be $C_5$–$C_8$ cycloalkenyl such as cyclopentenyl, cyclohexenyl or cyclooctenyl. Further, the halogen atom contained in $R^{11}$, may be a fluorine atom, a chlorine atom, a bromine atom or an iodine atom. The aryl group or the aryl moiety contained in $R^{11}$, may be phenyl, thienyl, furanyl, pyridyl, naphthyl, benzothienyl, benzofuranyl or quinolinyl.

The enopyranose derivatives of the formula (I) have stereoisomers, since the carbon atoms at the 1-, 2- and 5-positions of the pyranose ring are asymmetric carbon atoms, and such stereoisomers are also useful for the present invention.

Further, the salt of an enopyranose derivative of the formula (I) may be an acid addition salt with a mineral acid such as hydrochloric acid or sulfuric acid.

The enopyranose derivative of the formula (I) is preferably the following:

(1) the enopyranose derivative is a stereoisomer of the following formula (I-1) or (I-2):

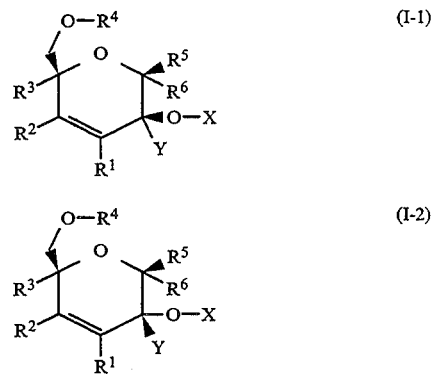

wherein $R^1$ to $R^6$, X and Y are as defined above.

(2) an enopyranose derivative of the formula (I-1) or (I-2) wherein $R^1$ is a hydrogen atom, alkyl which may be substituted, alkenyl or alkynyl, $R^2$ is a hydrogen atom or alkyl, each of $R^3$ and $R^6$ is a hydrogen atom, $R^4$ and $R^5$ together form a single bond, and X and Y are as defined above. The formula (I-1) is more preferable.

Enopyranose derivatives of the formula (I) include novel compounds. The present invention provides the following compounds as such novel compounds.

Namely, the present invention provides a compound of the following formula (I-1) or (I-2):

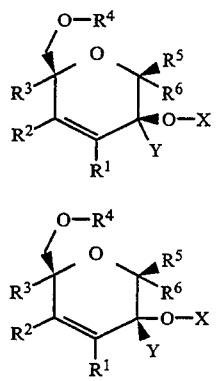

wherein $R^1$ is a hydrogen atom, alkyl which may be substituted, alkenyl, alkynyl, $-OSO_2R^7$, a halogen atom, $-OCOR^7$, $-NHCOR^8$, alkoxy, phenyl which may be substituted or a saccharose residue, $R^2$ is a hydrogen atom or alkyl, $R^3$ is a hydrogen atom or a halogen atom, $R^4$ and $R^5$ together form a single bond, $R^6$ is a hydrogen atom or alkyl which may be substituted, $R^7$ is alkyl or phenyl which may be substituted, $R^8$ is alkyl phenyl which may be substituted or benzyloxy, X is a hydrogen atom, alkyl which may be substituted, alkenyl which may be substituted, alkynyl which may be substituted, cycloalkyl which may be substituted, phenyl which may be substituted, pyridyl which may be substituted, furanyl which may be substituted, thienyl which may be substituted, formyl, $-COR^{11}$, $C(W^1)W^2R^{11}$ or $-SO_2R^{11}$, $R^{11}$ is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted, $W^1$ is an oxygen atom or a sulfur atom, $W^2$ is an oxygen atom, a sulfur atom or $-NH-$, Y is a hydrogen atom, alkyl which may be substituted, alkenyl which may be substituted or alkynyl which may be substituted, provided that the following cases are excluded:

① a case where in the formula (I-1) each of $R^1$, $R^2$, $R^3$, $R^6$ and X is a hydrogen atom, and Y is a hydrogen atom or alkyl which may be substituted, ② a case where in the formula (I-1) each of $R^1$, $R^2$, $R^3$, $R^6$ and Y is a hydrogen atom, X is acetyl, 3,5-dinitrobenzoyl or p-toluenesulfonyl, ③ a case where in the formula (I-1), each of $R^1$, $R^2$, $R^3$ and Y is a hydrogen atom, $R^6$ is alkyl which may be substituted, and X is a hydrogen atom or acetyl, and ④ a case where in the formula (I-2), each of $R^1$, $R^2$, $R^3$, $R^6$ and X is a hydrogen atom, and Y is methyl, ⑤ a case where in the formula (I-2), each of $R^1$, $R^2$, $R^3$, $R^6$ and Y is a hydrogen atom, and X is a hydrogen atom, methyl, benzyl, formyl, acetyl, benzoyl, 4-chlorobenzoyl, 3,5-dichlorobenzoyl, 4-nitrobenzoyl, 3,5-dinitrobenzoyl, 4-methoxybenzoyl, 3,5-dimethoxybenzoyl, methylsulfonyl or p-toluenesulfonyl, and ⑥ a case where in the formula (I-2), $R^1$ is p-toluenesulfonyloxy, each of $R^2$, $R^3$, $R^6$ and Y is a hydrogen atom, and X is a hydrogen atom, acetyl or p-toluenesulfonyl.

The following compounds are preferred as the compounds of the present invention.

(1) a compound of the formula (I-1) wherein $R^1$ is a hydrogen atom, alkyl which may be substituted, alkenyl or alkynyl, $R^2$ is a hydrogen atom or alkyl, each of $R^3$ and $R^6$ is a hydrogen atom, and $R^4$ and $R^5$ together form a single bond.

(2) a compound of the formula (I-1) wherein X is alkyl which may be substituted or $-COR^{11}$ ($R^{11}$ is as defined above), more preferably furfuryl or $-COR^{11}$ ($R^{11}$ is furanyl which may be substituted), $R^1$, $R^2$, $R^3$, $R^4$, $R^5$ and $R^6$ are as defined in the (1).

(3) a compound of the formula (I-1) wherein X is furancarbonyl or furfulyl.

(4) a compound of the formula (I-1) wherein Y is alkynyl which may be substituted. Among them, the following compounds or salts thereof are most preferable; 1,6-anhydro-3,4-dideoxy-2-O-(2-furancarbonyl)-β-D-threo-hex-3-enopyranose, 1,6-anhydro-3,4-dideoxy-2-O-(2-furancarbonyl)-3-methyl-β-D-threo-hex-3-enopyranose, 1,6-anhydro-3,4-dideoxy-2-C-ethynyl-2-O-(2-furancarbonyl)-β-D-threo-hex-3-enopyranose, 1,6-anhydro-3,4-dideoxy-2-O-(2-furfuryl)-β-D-threo-hex-3-enopyranose, 1,6-anhydro-3,4-dideoxy-2-O-(2-furfuryl)-3-methyl-β-D-threo-hex-3-enopyranose or 1,6-anhydro-3,4-dideoxy-2-C-ethynyl-2-O-(2-furfuryl)-β-D-threo-hex-3-enopyranose.

The enopyranose derivative of the formula (I) or its salt can be prepared by various methods. For example, 1,6-anhydro-3,4-dideoxy-β-D-glycero-hex-3-enopyranos-2-ulose is reduced to obtain 1,6-anhydro-3,4-dideoxy-β-D-threo-hex-3-enopyranose, which is then acylated, carbonated, carbamated, etherified or sulfonylated by a conventional method to obtain a desired compound. Otherwise, the 2-position of 1,6-anhydro-3,4-dideoxy-β-D-glycero-hex-3-enopyranos-2-ulose is alkylated, alkenylated or alkynylated by a conventional method to obtain a desired compound. Further, this 2-position reaction product may be acylated, carbonated, carbamated, etherified or sulfonylated as mentioned above to obtain a desired compound. On the other hand, 1,6-anhydro-3,4-dideoxy-β-D-erythro-hex-3-enopyranose can be obtained also by the above-mentioned reduction reaction. However, it can be prepared also by isomerization of the above-mentioned threo-isomer. Further, the product may be acylated, carbonated, carbamated, etherified or sulfonylated by a conventional method to obtain a desired compound.

Further, a compound of the following formula (II) may be used instead of 1,6-anhydro-3,4-dideoxy-β-D-glycero-hex-3-enopyranos-2-ulose.

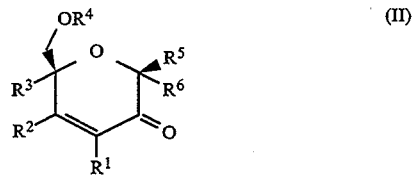

wherein $R^1$, $R^2$, $R^3$, $R^4$, $R^5$ and $R^6$ are as defined above.

The compound of the formula (II) is reduced, or alkylated, alkenylated or alkynylated by a conventional method and acylated, carbonated, carbamated, etherified or sulfonylated by a conventional method to obtain a desired compound. Otherwise, the compound of the formula (II) may be reduced and then isomerized, and acylated, carbonated, carbamated, etherified or sulfonylated by a conventional method to obtain a desired compound.

The compound of the formula (II) has an enantiomer (L-isomer), and the same reaction as mentioned above can be conducted by using this enantiomer.

These reactions may be carried out usually under an inert atmosphere such as nitrogen gas, helium gas or argon gas, whereby a side reaction and a decrease in the yield can be prevented. Now, common methods for production using these reactions will be described.

A. Reduction

A dry ether solution containing 1,6-anhydro-3,4-dideoxy-$\beta$-D-glycero-hex-3-enopyranos-2-ulose, or water or a solution of an alcohol such as methanol, ethanol or isopropanol containing it, is gradually added to at least 0.3 equivalent, preferably from 0.4 to 0.5 equivalent, of lithium aluminum hydride or sodium borohydride, respectively. The reaction mixture is stirred and reacted at a temperature of not higher than room temperature, preferably from −10° to 0° C., for from 0.5 to 2 hours. After adding a small amount of water, the reaction product is post-treated by a conventional method for purification and separation.

B. Acylation

A suitable acyl halide is gradually added in an amount of at least 1 equivalent, preferably from 1.5 to 2 equivalent, to a dry pyridine solution containing a reduced product of 1,6-anhydro-3,4-dideoxy-$\beta$-D-glycero-hex-3-enopyranos-2-ulose or its 2-position reaction product. The reaction mixture is stirred and reacted at a temperature of not higher than room temperature, preferably from −10° to 0° C., for from 0.5 to 2 hours. After adding a small amount of water, the reaction product is concentrated under reduced pressure to obtain a crude product, which is then purified and separated by a conventional method.

When acylation is directly conducted by means of a carboxylic acid instead of an acyl halide, from 1.5 to 2 equivalent of dicyclohexylcarbodiimide or diethylcarbodiimide, from 1.5 to 2 equivalent of a suitable carboxylic acid and from 0.1 to 0.2 equivalent of N,N-dimethylaminopyridine or diisopropylethylamine as a catalyst are added to a dry methylene chloride solution containing 1,6-anhydro-3,4-dideoxy-$\beta$-D-threo-hex-3-enopyranose, and the reaction is conducted under stirring at a temperature of from 0° to 30° C., preferably from 10° to 20° C., for from 6 to 12 hours. The reaction product is post-treated by a conventional method for purification and separation.

C. Carbonation

At least 2 equivalent, preferably from 2 to 3 equivalent, of a suitable chlorocarbonate is gradually added to a dry pyridine solution containing the reduced product of 1,6-anhydro-3,4-dideoxy-$\beta$-D-glycero-hex-3-enopyranos-2-ulose or its 2-position reaction product, and the reaction mixture is stirred and reacted at a temperature of from 0° to 30° C., preferably from 10° to 20° C., for from 6 to 12 hours. After adding a small amount of water, the reaction product is post-treated by a conventional method for purification and separation.

D. Carbamation

At least 1.3 equivalent, preferably from 1.5 to 2 equivalent, of a suitable isocyanate or isothiocyanate is gradually added to a dry toluene solution containing the reduced product of 1,6-anhydro-3,4-dideoxy-$\beta$-D-glycero-hex-3-enopyranos-2-ulose or its 2-position reaction product, and the mixture is stirred for from 10 to 15 minutes. Then, from 0.1 to 0.2 equivalent of the diisopropylethylamine, triethylamine or the like, or from 0.8 to 1.2 equivalent of sodium hydride, potassium hydride or the like is added thereto, and the mixture is further stirred and reacted. In the case of a reaction where triethylamine or the like is added, refluxing under heating is required.

In a case where phenyl isocyanate is used, diisopropylethylamine, triethylamine or the like is preferred, and in other cases, potassium hydride, sodium hydride or the like is preferred. After completion of the reaction, the reaction product is post-treated by a conventional method for purification and separation.

E. Etherification

The reduced product of 1,6-anhydro-3,4-dideoxy-$\beta$-D-glycero-hex-3-enopyranos-2-ulose or its 2-position reaction product is gradually added to a dry tetrahydrofuran suspension containing from 1.0 to 1.5 equivalent, preferably 1.3 equivalent, of a base such as sodium hydride or potassium hydride. The reaction mixture is stirred at a temperature of from 0° to 20° C., preferably from 0° to 10° C., for from 10 to 15 minutes, and then at least 1 equivalent, preferably from 1.3 to 1.5 equivalent, of a suitable organic halide is added thereto. The mixture is stirred and reacted at a temperature of from 10° to 30° C., preferably from 20° to 30° C. for from 6 to 12 hours. The above-mentioned organic halide may be selected depending upon the desired object, and it may, for example, be methyl iodide, butyl iodide or benzyl bromide. After adding a small amount of water, the reaction product is concentrated under reduced pressure to obtain a crude product, which is then subjected to purification and separation by a conventional method.

F. Sulfonylation

At least 1 equivalent, preferably from 1.5 to 2 equivalent, of a suitable sulfonyl halide is gradually added to a dry pyridine solution containing the reduced product of 1,6-anhydro-3,4-dideoxy-$\beta$-D-glycero-hex-3-enopyranos-2-ulose or its 2-position reaction product, and the reaction mixture is stirred and reacted at a temperature of from 10° to 30° C., preferably from 20° to 30° C., for from 6 to 12 hours. The above-mentioned sulfonyl halide is selected depending upon the desired object, and it may, for example, be p-toluenesulfonyl chloride, methanesulfonyl chloride. After adding a small amount of water, the reaction product was extracted with a solvent such as toluene. Then, the solvent is distilled off under reduced pressure to obtain a crude product, which is then subjected to purification and separation by a conventional method.

G. Alkylation, alkenylation or alkynylation

From 1.2 to 1.5 equivalent of an alkylation, alkenylation or alkynylation organic metal reagent, such as a suitable alkyl, alkenyl or alkynyl lithium or an alkyl, alkenyl or alkynyl magnesium bromide, is gradually added to a dry tetrahydrofuran solution containing 1,6-anhydro-3,4-dideoxy-$\beta$-D-glycero-hex-3-enopyranos-2-ulose. The reaction mixture is sintered and reacted at a temperature of from −78° to 0° C., preferably from −10° to 0° C., for from 0.5 to 1 hour. After adding a small amount of water, the reaction mixture is concentrated under reduced pressure to obtain a crude product, which is subjected to purification and separation by a conventional method.

H. Isomerization

From 1 to 2 equivalent, preferably 2 equivalent, of a metal salt of a carboxylic acid such as sodium benzoate, is added to a dry N,N-dimethylformamide solution of a p-toluenesulfonyl ester of the reduced product of 1,6-anhydro-3,4-dideoxy-β-D-glycero-hex-3-enopyranos-2-ulose or its 2-position reaction product, and the mixture is stirred and reacted at a temperature of from 100° to 150° C., preferably at a refluxing temperature, for 30 minutes. The reaction mixture is post-treated by a conventional method to remove the solvent and then dissolved in dry methanol. Then, from 1 to 2 equivalent, preferably 1.5 equivalent, of a base is added thereto, and the mixture is stirred and reacted at a temperature of from 0° to 30° C., preferably from 20° to 30° C., for 30 minutes. The above-mentioned base may, for example, be sodium hydroxide, potassium hydroxide or sodium methoxide. After completion of the reaction, the reaction product is post-treated by a conventional method for purification and separation.

The compound of the above-mentioned formula (II) can be produced by various methods. For example, the 3-position of 1,6-anhydro-3,4-dideoxy-β-D-glycero-hex-3-enopyranos-2-ulose is halogenated to obtain a desired compound, and this 3-position reaction product is alkylated, alkenylated, alkynylated or aryl-modified by a coupling reaction to obtain a desired compound. Further, 1,6-anhydro-3,4-dideoxy-β-D-glycero-hex-3-enopyranos-2-ulose or its 3-position, 4-position or 5-position substituted derivative is treated under an acidic condition to conduct ring opening of acetal and etherification at the 1-position simultaneously, or acylated at the 1-position and 6-position, to obtain a desired compound. Furthermore, the 6-position of the compound having the 1-position etherified, is etherified, acylated or silylated to obtain a desired compound. The obtained compound may be hydrolyzed for deacylation at the 1-position or at the 1- and 6-positions. On the other hand, using a natural saccharose such as glucose, galactose or mannose as the starting material, its 2-keto derivative is prepared by an oxidation reaction to obtain a desired enone derivative having an oxygen or nitrogen functional group at the 3-position.

In practical operation of these reactions, a side-reaction and a decrease in the yield can usually be prevented by conducting the reactions under an inert atmosphere such as nitrogen gas, helium gas or argon gas. Now, common methods for production using these reactions will be described.

A. Halogenation reaction

(A-1) Bromination

At least 0.9 equivalent, preferably from 1.5 to 2 equivalent, of bromine is slowly added at a temperature of not higher than 0° C., preferably from −10° to −15° C. to a carbon halide solution such as dry carbon tetrachloride or chloroform containing 1,6-anhydro-3,4-dideoxy-β-D-glycero-hex-3-enopyranos-2-ulose. The reaction mixture is stirred and reacted at a temperature of not higher than 0° C., preferably from −10° to −15° C., for from 10 to 30 minutes. Then, at least 5 equivalent, preferably from 8 to 10 equivalent, of a base such as pyridine, triethylamine or diisopropylethylamine is added thereto, and the mixture is stirred and reacted for 12 hours. After adding water, the reaction solution was post-treated by a conventional method for purification and separation.

(A-2) Iodination

A dry pyridine-carbon tetrachloride solution containing at least 5 equivalent, preferably from 8 to 10 equivalent, of iodine, is gradually added at a temperature of not higher than 5° C., preferably from 0° to 5° C., to a dry pyridine-carbon tetrachloride solution containing 1,6-anhydro-3,4-dideoxy-β-D-glycero-hex-3-enopyranos-2-ulose. The reaction mixture is stirred and reacted at room temperature preferably from 15° to 25° C., for two hours. After adding ethyl acetate, the reaction mixture is post-treated by a conventional method for purification and separation. With respect to this method, the synthesis was conducted in accordance with the method by Carl R. Johnson et at. (Tetrahedron Lett., 33, 917–918, (1992)). With respect to the synthesis of an α-iodine derivative directly from an enone, there are other methods by John M. Mcintosh (Can. J. Chem., 49, 3045–3047, (1971)) and by T. H. Kim et al. (Chem. Express, 5, 221, (1990)).

B. Coupling reaction

From 0.01 to 0.3 equivalent, preferably from 0.05 to 0.15 equivalent, of copper(I) iodide, from 0.01 to 0.3 equivalent, preferably from 0.05 to 0.15 equivalent, of triphenylarsine and from 0.01 to 0.1 equivalent, preferably from 0.03 to 0.07 equivalent, of a palladium catalyst such as dichlorobis(benzonitrile)palladium(II) were added to a dry 1-methyl-2-pyrrolidinone solution containing 1,6-anhydro-3,4-dideoxy-3-iodo-β-D-glycero-hex-3-enopyranos-2-ulose, to conduct the reaction. To the reaction mixture, an organotin compound or an organozinc compound is added, and the reaction is conducted at a temperature of from 0° to 100° C., preferably from 25° to 80° C., for from 1 to 10 hours, preferably from 2 to 6 hours. After adding ethyl acetate, the reaction product was post-treated by a conventional method for purification and separation. With respect to this method, the synthesis can be conducted in accordance with the method by C. R. Johnson et al. (Tetrahedron Lett., 33, 919–922 (1992)). Further, in a case where $R^1$ in the formula (II) is alkyl which may be substituted, the following method may be employed. Namely, 1,6-anhydro-3-bromo-3,4-dideoxy-β-D-glycero-hex-3-enopyranos-2-ulose is reacted together with at least 1 equivalent of ethylene glycol and a catalytic amount of p-toluenesulfonic acid at a refluxing temperature of a solvent such as benzene or toluene to obtain 1,6-anhydro-3-bromo-3,4-dideoxy-β-D-glycero-hexo-3-enopyranos-2-ulose ethylene acetal having the carbonyl group at the 2-position of the pyranose ring protected. Then, this product is reacted in a solvent such as tetrahydrofuran together with at least one equivalent of n-butyl lithium and at least one equivalent of an alkyl iodide at a reaction temperature of from −60° to −80° C. After the reaction, the protecting group at the 2-position of the pyranose ring is removed by a catalytic amount of p-toluenesulfonic acid at a refluxing temperature of tetrahydrofuran and water. Instead of the above-mentioned alkyl iodide, various ketones or aldehydes may be employed. In such a case, a compound wherein $R^1$ is an alkyl group substituted by a hydroxyl group, will be obtained. Further, if an alcohol such as methanol is used as a solvent in the reaction for removing the protecting group, the hydroxyl moiety of a hydroxyl-substituted alkyl group can be converted to an alkoxy group such as methoxy. Further, the hydroxy moiety of the hydroxyl-substituted alkyl group may be aminated by a conventional method.

C. Ring opening reaction of acetal

From 0.05 to 0.5 equivalent, preferably from 0.08 to 0.15 equivalent, of a Lewis acid such as sulfuric acid or boron trifluoride etherate is gradually added at a temperature of from −20° C. to 15° C., preferably from −10° C. to 0° C., to a suitable acid anhydride containing 1,6-anhydro-3,4-dideoxy-β-D-glycero-hex-3-enopyranos-2-ulose or its 1-position, 3-position, 4-position or 5-position substituted derivative or to a dry chloroform solution of such an acid anhydride. The reaction mixture is stirred for 10 minutes to 2 hours, preferably from 15 to 30 minutes. Then, the reaction solution is added to an ice-cooled saturated sodium bicarbonate solution and then treated by a conventional method for purification and separation (Carbohydr. Res., 71, 169–191 (1979)).

On the other hand, to prepare a 1-alkoxy derivative, from 1 to 5%, preferably from 3 to 4%, of concentrated sulfuric acid is added to a solution of a corresponding alcohol such as methanol, ethanol or propanol, and the mixture is stirred at a temperature of from 10° to 30° C., preferably from 15° to 25° C., for from 5 to 48 hours, preferably from 12 to 36 hours. The reaction solution is neutralyzed with a base such as sodium hydrogencarbonate and then treated by a conventional method for purification and separation. The alcohol at the 6-position formed, can be converted by a conventional method such as etherification or acylation to a corresponding derivative.

D. Hydrolysis

From 0.05 to 0.3 equivalent, preferably from 0.1 to 0.15 equivalent, of a base such as lithium hydroxide, sodium hydroxide or potassium hydroxide, is added to a solution of water or an alcohol such as methanol, ethanol or isopropanol, containing 1,6-di-O-acyl-3,4-dideoxy-α-D-glycero-hex-3-enopyranos-2-ulose or its 1-position, 3-position, 4-position or 5-position substituted derivative, and the mixture is stirred at a temperature of from 10° to 30° C., preferably from 15° to 25° C., for from 10 to 45 minutes, preferably from 20 to 30 minutes. Ethyl acetate is added to the reaction product, and then the precipitate is removed by filtration. The filtrate is concentrated under reduced pressure to obtain a product, which is subjected to purification and separation by a conventional method.

E. Oxidation reaction

From 1 to 10 equivalent, preferably from 2 to 5 equivalent, of pyridinium chlorochromate is added to a dry methylene chloride solution containing 3,4-dideoxy-hex-3-enopyranose or its derivative, and the mixture is stirred and reacted at a temperature of from 0° to 40° C., preferably from 10° to 20° C., for from 1 to 20 hours, preferably from 2 to 12 hours. Diethyl ether is added to the reaction product, and the mixture is filtered through silica gel, and the filtrate is concentrated to obtain a crude product. The crude product is subjected to purification and separation by a conventional method.

The compounds of the formula (II) contain compounds which have not been disclosed in literatures. For example, a compound of the formula (II')

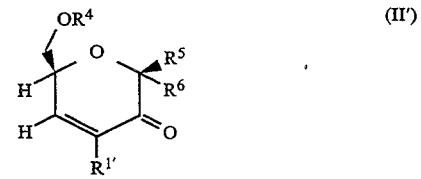

wherein $R^{1'}$ is alkyl which may be substituted, alkenyl, alkynyl, $-OSO_2R^7$, a halogen atom, phenyl which may be substituted, or a saccharose residue, and $R^4$, $R^5$, $R^6$ and $R^7$ are as defined above, excluding a case wherein $R^{1'}$ is a bromine atom, $R^4$ and $R^5$ together form a single bond, and $R^6$ is a hydrogen atom, or its salt, is a novel compound.

Further, immuno-suppressive effects are observed also with the compounds of the formula (II).

The enone derivatives of the formula (II) will be presented in Tables 1 and 2.

TABLE 1

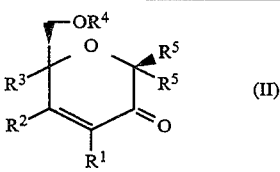

(II)

| Intermediate No. | $R^1$ | $R^2$ | $R^3$ | $R^4$ | $R^5$ | $R^6$ |
|---|---|---|---|---|---|---|
| 1 | H | H | H | Single bond | | H |
| 2 | $CH_3$ | H | H | Single bond | | H |
| 3 | $-OSO_2-\langle\bigcirc\rangle-CH_3$ | H | H | Single bond | | H |
| 4 | Br | H | H | Single bond | | H |
| 5 | I | H | H | Single bond | | H |
| 6 | $-OCOCH_3$ | H | H | Single bond | | H |
| 7 | H | H | H | Single bond | | $-CH_2OH$ |
| 8 | H | H | H | Single bond | | $CH_3$ |

TABLE 1-continued $$\text{(II)}$$

| Intermediate No. | $R^1$ | $R^2$ | $R^3$ | $R^4$ | $R^5$ | $R^6$ |
|---|---|---|---|---|---|---|
| 9 | (bicyclic structure with O, O, cyclohexene, methyl) | H | H | Single bond | | H |
| 10 | H | H | H | H | H/OH | OH/H |
| 11 | H | H | H | H | H | —$OCH_3$ |
| 12 | H | H | H | —$COCH_3$ | H | —$OCH_3$ |
| 13 | H | H | H | $SitBuMe_2$ | H | —$OCH_3$ |
| 14 | H | H | H | H | —$OCH_3$ | H |
| 15 | H | H | H | —$COCH_3$ | H | —$OCOCH_3$ |
| 16 | Br | H | H | —$COCH_3$ | H | —$OCOCH_3$ |
| 17 | H | H | H | —$COCH_3$ | H/OH | OH/H |
| 18 | Br | H | H | —$COCH_3$ | H/OH | OH/H |
| 19 | H | H | H | —$COC_2H_5$ | H | —$OCOC_2H_5$ |
| 20 | $CH_3$ | H | H | H | H | —$OCH_3$ |
| 21 | H | H | H | $CH_3$ | —$OCH_3$ | H |
| 22 | H | H | H | —CO-phenyl | —$OCH_3$ | H |
| 23 | H | H | H | Tr | H | —$OCH_3$ |
| 24 | H | H | H | —$COCH_3$ | —$OC_4H_9t$ | H |
| 25 | H | H | H | H | —$OC_4H_9t$ | H |
| 26 | H | H | H | —$COCH_3$ | —$OC_3H_7i$ | H |

TABLE 2

| Intermediate No. | $R^1$ | $R^2$ | $R^3$ | $R^4$ | $R^5$ | $R^6$ |
|---|---|---|---|---|---|---|
| 27 | H | H | H | $CH_3$ | H/OH | OH/H |
| 28 | H | H | H | $SitBuMe_2$ | $OC_2H_5$ | H |
| 29 | H | H | H | $SitBuMe_2$ | $OC_4H_9t$ | H |
| 30 | H | H | H | —CO-C$_6$H$_4$-$NO_2$ | $OCH_3$ | H |
| 31 | H | H | H | —$CH(CH_3)OC_2H_5$ | $OCH_3$ | H |
| 32 | —$NHCOCH_3$ | H | H | —$COCH_3$ | $OCH_3$ | H |
| 33 | —$OCOCH_3$ | H | H | —$COCH_3$ | $OCH_3$ | H |
| 34 | —OCO-phenyl | H | Br | —CO-phenyl | —OCO-phenyl | H |
| 35 | —OCO-phenyl | H | H | —CO-phenyl | —O-cyclohexyl | H |
| 36 | —$OCOC_4H_9t$ | H | H | —$COC_4H_9t$ | —$OCH_3$ | H |

TABLE 2-continued

| Intermediate No. | $R^1$ | $R^2$ | $R^3$ | $R^4$ | $R^5$ | $R^6$ |
| --- | --- | --- | --- | --- | --- | --- |
| 37 | —NHCOOCH$_2$—C$_6$H$_5$ | H | H | H | —OCH$_3$ | H |
| 38 | —OCH$_3$ | H | H | CH$_3$ | —OCH$_2$—(tetrahydropyran: OMe, MeO, OMe, OMe substituents) | |
| 39 | —OCOCH$_3$ | H | H | —COCH$_3$ | —OCOCH$_3$ | H |
| 40 | H | CH$_3$ | H | —CO—C$_6$H$_5$ | —OC$_2$H$_5$ | H |
| 41 | H | CH$_3$ | H | Tr | —OC$_2$H$_5$ | H |
| 42 | —C$_6$H$_4$—CH$_3$ | H | H | | Single bond | H |
| 43 | H | CH$_3$ | H | | Single bond | H |
| 44 | —CH=CH$_2$ | H | H | | Single bond | H |
| 45 | —C≡CH | H | H | | Single bond | H |
| 46 | —CH$_2$CH$_3$ | H | H | | Single bond | H |
| 47 | —(CH$_2$)$_3$CH$_3$ | H | H | | Single bond | H |
| 48 | —CH$_2$OCH$_3$ | H | H | | Single bond | H |

H/OH and OH/H for $R^5$ and $R^6$ mean that either $R^5$ or $R^6$ is an OH group.

SitBuMe$_2$ represents a tert-butyl dimethylsilyl group, C$_4$H$_9$t represents a tert-butyl group, and C$_3$H$_7$i represents an iso-propyl group.

Tr represents a triphenylmethyl group, and —⟨H⟩ represents a cyclohexyl group.

INTERMEDIATE PREPARATION EXAMPLE 1

Preparation of 1,6-anhydro-3,4-dideoxy-3-iodo-β-D-glycero-hex-3-enopyranos-2-ulose (Intermediate No. 5)

150 ml of a dry pyridine-carbon tetrachloride (1:1) solution containing 40 g of iodine, was gradually added at 0° C. to 150 ml of a dry pyridine-carbon tetrachloride (1:1) solution containing 5 g of 1,6-anhydro-3,4-dideoxy-β-D-glycero-hex-3-enopyranos-2-ulose (disclosed in U.S. Pat. No. 3,926,947) under an inert atmosphere of nitrogen gas. The mixture was stirred at room temperature for two hours. Then, disappearance of the starting material was confirmed by thin layer chromatography, and 200 ml of ethyl acetate was added thereto. The mixture was washed twice with 200 ml of a saturated sodium chloride aqueous solution and once with 200 ml of 20% sodium thiosulfate. The organic layer was dried over anhydrous sodium sulfate, and then the solvent was distilled off under reduced pressure. The obtained syrup crude product was purified by silica gel column chromatography (ethyl acetate: hexane=1:3) to obtain 6.1 g of the desired product (Intermediate No. 5) as slightly yellow crystals. The NMR analytical data and physical data of this product are as follows.

$^1$H NMR(CDCl$_3$, 400MHz): 3.81(1H,d,J=6.8Hz); 3.87(1H,dd,J=6.8,5.0Hz); 4.93(1H,t,J=5.0Hz); 5.57(1H,s); 7.96(1H,d,J=5.0Hz)

m.p. 66°–67° C.

INTERMEDIATE PREPARATION EXAMPLE 2

Preparation of 1,6-anhydro-3,4-dideoxy-3-methyl-β-D-glycero-hex-3-enopyranos-2-ulose (Intermediate No. 2)

5.3 g of tetramethyltin was added to 20 ml of a dry N-methylpyrrolidinone solution containing a mixture comprising 5 g of 1,6-anhydro-3,4-dideoxy-3-iodo-β-D-glycero-hex-3-enopyranos-2-ulose, 0.4 g of copper(I) iodide, 0.6 g of triphenylarsine and 0.4 g of dichlorobis(-benzonitrile)palladium(II) under an inert atmosphere of nitrogen gas. The mixture was stirred at 80° C. for 4 hours. Then, 200 ml of ethyl acetate was added thereto, and the mixture was washed three times with 100 ml of a 10% potassium fluoride aqueous solution. The organic layer was dried over anhydrous sodium sulfate, and then the solvent was distilled off under reduced pressure. The obtained syrup product was purified by silica gel column chromatography (ethyl acetate: hexane=1:3) and then distilled under reduced pressure to obtain 1.61 g of the desired product (Intermediate No. 2) as a colorless transparent liquid. The NMR analytical data of this product are as follows.

$^1$H NMR(CDCl$_3$,400MHz): 1.79(3H, s); 3.68(1H,d,J=6.8Hz); 3.83(1H,dd,J=6.8,4.8Hz); 4.95(1H,t,J=4.8Hz); 5.36(1H,s); 6.96(1H,dq,J=4.8,1.6Hz) b.p. 150°–170° C. (40mmHg)

The following compounds were prepared in the same manner as in the above Intermediate Preparation Example 2, and their physical properties will be given.

Intermediate No. 42

$^1$H NMR(CDCl$_3$,400MHz): 2.36(3H,s); 3.85(1H,d,J=6.6Hz); 3.95(1H,dd,J=6.6,4.8Hz); 5.15(1H,t,J=4.8Hz); 5.50(1H,s); 7.19(2H,br,d,J=8.1Hz); 7.23 (1H,d,J=4.8Hz); 7.32(2H,br,d,J=8.1Hz)
m.p. 117°–119° C.

Intermediate No. 9

$^1$H NMR(CDCl$_3$,400MHz): 1.82(1H,dt, J=11.5,4.8Hz); 1.90(1H,m); 1.98(1H,dt,J=11.5,3.3Hz); 2.22(1H, m); 2.64(1H,dddd,J=20.0,3.5,3.5,3.5Hz); 3.15(1H,m); 3.62(1H,d,J=6.9Hz); 3.68(1H,d,J=7.3Hz); 3.79(1H,dd,J=7.3,4.7Hz); 3.87(1H,dd,J=6.9,4.31Hz); 4.40(1H,d,J=4.7Hz); 5.01(1H,t,J=4.7Hz); 5.17(1H,s); 5.35(1H,s); 6.80(1H,dd,J=4.7,1.2Hz); 6.93(1H,q,J=3.5Hz)

INTERMEDIATE PREPARATION EXAMPLE 3

Preparation of methyl 3,4-dideoxy-3-methyl-α-D-glycero-hex-3-enopyranos-2-ulose (Intermediate No. 20)

0.1 ml of concentrated sulfuric acid was added to 30 ml of a dry methanol solution containing 500 mg of 1,6-anhydro-3,4-dideoxy-3-methyl-β-D-glycero-hex-3-enopyranos-2-ulose (Intermediate No. 2), and the mixture was stirred at room temperature for 48 hours. Then, 30 ml of a saturated sodium hydrogencarbonate aqueous solution was added thereto, and the mixture was stirred at room temperature for 15 minutes and then concentrated under reduced pressure. Then, 200 ml of ethyl acetate was added thereto, and the mixture was washed three times with 200 ml of a saturated sodium chloride aqueous solution. The organic layer was dried over anhydrous sodium sulfate, and then the solvent was distilled off under reduced pressure. The obtained syrup crude product was purified by silica gel column chromatography (ethyl acetate: hexane=2:3) to obtain 350 mg of the desired compound (Intermediate No. 20) as a colorless liquid. The NMR analytical data of this product are as follows. $^1$H NMR(CDCl$_3$,400MHz): 1.86(3H,m); 1.95(1H,t,J=6.0Hz); 3.54(3H,s); 3.76(1H,ddd,J=11.2,6.8,6.0Hz); 3.84(1H,ddd,J=11.2,6.0,3.6Hz); 4.63(1H,m); 4.80(1H,s); 6.68(1H,m)

INTERMEDIATE PREPARATION EXAMPLE 4

Preparation of 1,6-di-O-propionyl-3,4-dideoxy-α-D-glycero-hex-3-enopyranos-2-ulose (Intermediate No. 19)

100 mg of 1,6-anhydro-3,4-dideoxy-β-D-glycero-hex-3-enopyranos-2-ulose was dissolved in 3 ml of propionic anhydride, and the solution was cooled to −20° C. Then, 0.06 ml of concentrated sulfuric acid was added thereto, and the mixture was stirred for 30 minutes. Then, the reaction mixture was added to 100 ml of an ice-cooled saturated sodium hydrogencarbonate aqueous solution. The mixture was stirred for 30 minutes and then extracted with 100 ml of ethyl acetate. The extract was washed three times with 100 ml of a saturated sodium chloride aqueous solution. The organic layer was dried over anhydrous sodium sulfate, and the solvent was distilled off under reduced pressure. The obtained syrup crude product was purified by silica gel column chromatography (ethyl acetate: hexane=1:2) to obtain 100 mg of the desired product (Intermediate No. 19) as a colorless transparent liquid. The NMR analytical data of this product are as follows.

Intermediate No. 19

$^1$H NMR(CDCl$_3$,400MHz): 1.14(3H,t,J=5.2Hz); 1.16(3H,t,J=5.2Hz); 2.38(4H,m); 4.22(1H,dd,J=11.4,4.6Hz); 4.41(1H,dd,J=11.4,4.7Hz); 4.81(1H,m,); 6.20(1H,s); 6.28(1H,dd,J=10.6,2.4Hz); 7.05(1H,dd,J=10.6,1.9Hz)

The following compound was prepared in the same manner as in the above Intermediate Preparation Example 4, and its physical properties will be given.

Intermediate No. 16

$^1$H NMR(CDCl$_3$,400MHz): 2.10(3H,s); 2.13(3H,s); 4.20(1H,dd,J=11.4,5.0Hz); 4.38(1H,dd,J=11.4,5.0Hz); 4.88(1H,td,J=5.0,1.9Hz); 6.34(1H,s); 7.43(1H,d,J=1.9Hz)

INTERMEDIATE PREPARATION EXAMPLE 5

Preparation of 6-O-acetyl-3-bromo-3,4-dideoxy-D-glycero-hex-3-enopyranos-2-ulose (Intermediate No. 18)

200 mg of 1,6-di-O-acetyl-3-bromo-3,4-dideoxy-α-D-glycero-hex-3-enopyranos-2-ulose prepared in the same manner as in the above Intermediate Preparation Example 4 from 1,6-anhydro-3-bromo-3,4-dideoxy-β-D-glycero-hex-3-enopyranos-2-ulose (Intermediate No. 4) prepared by the method disclosed in Carbohydrate Research (1981), Vol. 93, 284–287, was dissolved in 6 ml of tetrahydrofuran-water (5:1), and 70 mg of lithium hydroxide monohydrate was added thereto. The mixture was stirred at room temperature for 30 minutes. To the reaction solution, 100 ml of ethyl acetate was added. The mixture was washed three times with 100 ml of a saturated sodium chloride aqueous solution. The organic layer was dried over anhydrous sodium sulfate, and then the solvent was distilled off under reduced pressure. The obtained syrup crude product was purified by thin layer chromatography for separation (NO-5744, manufactured by Merck, ethyl acetate: hexane=1:1) to obtain 40 mg of the desired product (Intermediate No. 18) as a slightly yellow liquid. The NMR analytical data of this product are as follows.

$^1$H NMR(CDCl$_3$,400MHz): 2.12(0.9H,s); 2.13(0.1H,s); 4.24(0.1H,dd,J=11.2,5.0Hz); 4.26(0.9H,dd,J=11.5,5.0Hz); 4.35(0.9H,dd,J=11.5,5.0Hz); 4.47 (0.1H,dd,J=11.2,6.5Hz); 4.78(0.1H,dddd,J=6.5,5.0,1.9,1.0Hz); 5.00(0.9H,td, J=5.0,2.2Hz); 5.31(0.1H,br,s); 5.46(0.9H,br,s); 7.38(0.9H,d,J=2.2Hz); 7.44(0.1H,d,J=1.9Hz)

The following compound was prepared in the same manner as the above Intermediate Preparation Example 5, and its physical properties will be given.

Intermediate No. 17

$^1$H NMR(CDCl$_3$,400MHz): 2.09(2.25H,s); 2.10(0.75H,s); 4.26(0.25H,dd,J=11.5,5.0Hz); 4.27(0.75H,dd,J=11.5,4.3Hz);

4.34(0.75H,dd,J=11.5,5.3Hz);
4.42(0.25H,dd,J=11.5,6.2Hz); 4.79(0.25H,m):
4.93(0.75H,m); 5.19(0.25H,br, d,J=5.7Hz);
5.26(0.75H,br,d,J=3.3Hz);
6.19(0.75H,dd,J=10.4,2.5Hz);
6.27(0.25H,dd,J=10.0,2.8Hz);
6.99(0.75H,dd,J=10.4,1.7Hz);
6.99(0.25H,dd,J=10.0,1.9Hz)

INTERMEDIATE PREPARATION EXAMPLE 6

Preparation of
1,6-anhydro-3-O-p-toluenesulfonyl-4-deoxy-$\beta$-D-glycero-hex-3-enopyranos-2-ulose (Intermediate No. 3)

360 mg of pyridinium chlorochromate was added to 20 ml of a dry methylene chloride solution containing 50 mg of 1,6-anhydro-3-O-p-toluenesulfonyl-4-deoxy-$\beta$-D-erythro-hex-3-enopyranose, and the mixture was stirred at room temperature for 48 hours. Disappearance of the starting material was confirmed by thin layer chromatography, and then 60 ml of diethyl ether was added thereto. The mixture was further stirred at room temperature for 15 minutes. Then, the reaction mixture was filtered by silica gel and washed with 200 ml of diethyl ether. The washing solution was concentrated under reduced pressure together with the filtrate. The obtained syrup crude product was purified by silica gel column chromatography (ethyl acetate: hexane=1:2) to obtain 34 mg of the desired product (Intermediate No. 3) as a colorless transparent liquid. The NMR analytical data of this product are as follows.

$^1$H NMR(CDCl$_3$,400MHz): 2.45(3H,s); 3.83(1H,d,J=7.2Hz); 3.92(1H,dd,J =7.2,4.8Hz); 5.14(1H,t,J=4.8Hz); 5.36(1H,s); 7.17(1H,d,J=4.8Hz); 7.35(2H, br,d,J=8.0Hz); 7.82(2H,dt,J=8.8,2.0Hz)
m.p. 81°–86° C.

INTERMEDIATE PREPARATION EXAMPLE 7

Preparation of
1,6-anhydro-3,4-dideoxy-4-methyl-$\beta$-D-glycero-hex-3-enopyranos-2-ulose (Intermediate No. 43)

1 ml of a tetrahydrofuran solution containing 300 mg of 1,6-anhydro-3,4-dideoxy-4-C-methyl-$\beta$-D-erythro-hexopyranose-2-ulose (disclosed in Carbohydrate Res., 71, (1979) 169), was added at −78° C. to a lithium amide solution prepared by a conventional method from 0.45 ml of diisopropylamine and 1.75 ml of butyl lithium in 25 ml of dry tetrahydrofuran, under an inert atmosphere of nitrogen gas. The mixture was stirred for one hour, and then 3 ml of a tetrahydrofuran solution containing 500 mg of phenyl serenyl chloride and 0.75 ml of phosphoric acid hexamethyl triamide, was added. The mixture was stirred at −78° C. for 30 minutes. Then, a saturated ammonium chloride aqueous solution was added thereto, and the solvent was distilled off under reduced pressure. Then, the mixture was extracted with ethyl acetate. The extract was washed twice with a saturated sodium chloride aqueous solution and then dried over anhydrous sodium sulfate. The solvent was distilled off under reduced pressure to obtain a syrup crude product. This crude product was purified by silica gel column chromatography (ethyl acetate: hexane=1:10) to obtain 106 mg of a serenium derivative.

The serenium derivative obtained by the above reaction was dissolved in 20 ml of dry methylene chloride under an inert atmosphere of nitrogen gas, and 60 mg of m-chloroperbenzoic acid was added thereto at −78° C. The mixture was stirred for 20 minutes and then a saturated sodium hydrogencarbonate aqueous solution was added. The mixture was extracted twice with methylene chloride. The organic layers were put together and washed twice with a saturated sodium chloride aqueous solution and then dried over anhydrous sodium sulfate. The solvent was distilled off under reduced pressure. The obtained syrup crude product was purified by silica gel thin layer chromatography (methylene chloride) to obtain 1.7 mg of desired 1,6-anhydro-3,4-dideoxy-4-methyl-$\beta$-D-glycero-hex-3-enopyranos-2-ulose (Intermediate No. 43) as a colorless transparent liquid. The NMR analytical data of this product are as follows.

$^1$H NMR(CDCl$_3$,400MHz): 2.08(3H,d,J=1.2Hz); 3.71(1H,d,J=6.8Hz); 3.91(1H,dd,J=6.8,4.8Hz); 4.80(1H,d,J=4.8Hz); 5.32(1H,d,J=1.2Hz); 5.87(1H,m)

INTERMEDIATE PREPARATION EXAMPLE 8

Preparation of
1,6-anhydro-3,4-dideoxy-3-ethyl-$\beta$-D-glycero-hex-3-enopyranos-2-ulose (Intermediate No. 46)

(1) 22 g of 1,6-anhydro-3-bromo-3,4-dideoxy-$\beta$-D-glycero-hex-3-enopyranos-2-ulose was dissolved in 500 ml of dry benzene, and 66 g of ethylene glycol and 3 g of p-toluenesulfonic acid monohydrate were added thereto. The mixture was refluxed under heating while removing formed water. 19 hours later, disappearance of the starting material was confirmed by TLC, and the reaction mixture was cooled to room temperature. Then, 500 ml of ethyl acetate was added thereto, and the mixture was washed three times with 200 ml of a saturated sodium chloride aqueous solution. The organic layer was dried over anhydrous sodium sulfate, and then the solvent was distilled off under reduced pressure. The obtained crude crystals were purified by silica gel column chromatography (ethyl acetate: hexane=1:1) to obtain 20 g of 1,6-anhydro-3-bromo-3,4-dideoxy-$\beta$-D-glycero-hex-3-enopyranos-2-ulose ethylene acetal as white crystals. The NMR analytical data of this product are as follows.

$^1$H NMR(CDCl$_3$,400MHz): 3.71(1H,dd,J=6.8,4.4Hz); 3.79(1H,d,J=6.8Hz); 4.04(1H,m); 4.17(1H,m); 4.28(2H,m); 4.75(1H,t,J=4.4Hz); 5.28(1H,s); 6.60(1H,d,J=4.4Hz)
m.p. 111°–112° C.

(2) 3 g of 1,6-anhydro-3-bromo-3,4-dideoxy-$\beta$-D-glycero-hex-3-enopyranos-2-ulose ethylene acetal obtained in the above step (1) was dissolved in 200 ml of dry tetrahydrofuran. Then, 1.2 equivalent of n-butyl lithium was added thereto under stirring at −78° C. under a nitrogen atmosphere. The mixture was stirred for 20 minutes, and then 10 ml of a dry tetrahydrofuran solution containing 1.9 ml of ethyl iodide and 5.2 ml of hexamethyl phosphoamide, was added thereto. The mixture was stirred for 30 minutes, and then gradually heated to room temperature. Completion of the reaction was confirmed by TLC, and then a small amount of water was added. The solvent was distilled off under reduced pressure. To the residue, 300 ml of ethyl acetate was added, and the mixture was washed three times with 100 ml of a saturated sodium chloride aqueous solution. The organic layer was dried over anhydrous sodium sulfate. The solvent was distilled off under reduced pressure, and then the obtained syrup crude product was purified by silica gel column chromatography (ethyl acetate: hexane =1:2) to obtain 1.48 g of 1,6-anhydro-3,4-dideoxy-3-ethyl-$\beta$-D-glycero-hex-3- enopyranos-2-ulose ethylene acetal as white crystals. The NMR analytical data of this product are as follows.

$^1$H NMR(CDCl$_3$,400MHz): 1.03(3H,t,J=7.2Hz); 2.03(1H,m); 2.11(1H,dqd, J=16.6,7.2,2.0Hz); 3.70(2H,m); 4.00–4.10(3H,m); 4.16(1H,m); 4.74(1H,m); 5.19(1H,s); 5.94(1H,dt,J=4.4,2.0Hz)

(3) 1.47 g of 1,6-anhydro-3,4-dideoxy-3-ethyl-β-D-glycero-hexo-3-enopyranos-2-ulose ethylene acetal obtained in the above step (2) was dissolved in 150 ml of dry tetrahydrofuran-water (2:1), and 2 g of p-toluenesulfonic acid monohydrate was added thereto. The obtained mixture was refluxed under heating for two hours, and then the solvent was distilled off under reduced pressure. The obtained syrup crude product was dissolved in 200 ml of ethyl acetate, and the solution was washed three times with 100 ml of a saturated sodium chloride aqueous solution. Then, the organic layer was dried over anhydrous sodium sulfate. The solvent was distilled off under reduced pressure, and the obtained crude product was purified by silica gel column chromatography (ethyl acetate: hexane=1:2) to obtain 1.1 g of the desired product (Intermediate No. 46). The NMR analytical data of this product are as follows.

$^1$H NMR(CDCl$_3$,400MHz): 1.16(3H,t,J=7.6Hz); 2.35(2H,qd,J=7.6,1.5Hz); 3.81(1H,d,J=6.6Hz); 3.95(1H,dd,J=6.6,4.6Hz); 5.12(1H,t,J=4.6Hz); 5.48(1H,s); 7.03(1H,dt,J=4.6,1.5Hz)

The following compound was prepared in the same manner as in the above Intermediate Preparation Example 8 and its physical properties will be given.

Intermediate No. 47

$^1$H NMR(CDCl$_3$,400MHz): 0.90(3H,t,J=7.2Hz); 1.30–1.50(4H,m); 2.17(1H, ddd,J=14.4,6.8,1.6Hz); 2.23(1H,dd,J=14.4,6.8Hz); 3.69(1H,d,J=6.8Hz); 3.86(1H,dd,J=6.8,4.4Hz); 4.98(1H,t,J=4.4Hz); 5.36(1H,s); 6.92(1H,dt,J=4.4,1.6Hz)

INTERMEDIATE PREPARATION EXAMPLE 9

Preparation of 1,6-anhydro-3,4-dideoxy-3-methoxymethyl-β-D-glycero-hex-3-enopyranos-2-ulose (Intermediate No. 48)

(1) 1.65 g of 1,6-anhydro-3-bromo-3,4-dideoxy-β-D-glycero-hex-3-enopyranos-2-ulose ethylene acetal obtained in the above Intermediate Preparation Example 8 (1), was dissolved in 200 ml of dry tetrahydrofuran, and the solution was cooled to −78° C. Then, 5 ml (1.6N) of n-butyl lithium was gradually added thereto, and the mixture was further stirred for 20 minutes. To the obtained reaction mixture, formaldehyde gas was introduced in large excess, and the temperature was raised to room temperature. Termination of the reaction was confirmed by TLC, and then the reaction mixture was filtered through Celite® to remove the precipitate. The filtrate was concentrated under reduced pressure, and the obtained syrup crude product was purified by silica gel column chromatography (ethyl acetate: hexane=1:1) to obtain 0.7 g of 1,6-anhydro-3,4-dideoxy-3-hydroxymethyl-β-D-glycero-hex-3-enopyranos-2-ulose ethylene acetal. The NMR analytical data of this product are as follows.

$^1$H NMR(CDCl$_3$,400MHz): 2.04(1H,br,s); 3.73(2H,m); 4.00–4.20(5H,m); 4.17(1H,dd,J=12.0,1.2Hz); 4.79(1H,m); 5.19(1H,s); 6.32(1H,dt,J=4.8,1.2Hz)

2 g of p-toluene sulfonic acid monohydrate was added to 150 ml of a methanol solution containing 2.8 g of 1,6-anhydro-3,4-dideoxy-3-hydroxymethyl-β-D-glycero-hex-3-enopyranos-2-ulose obtained in the above step (1), and the mixture was refluxed under heating for one hour. Disappearance of the starting material was confirmed by TLC, and then the solvent was distilled off under reduced pressure. The obtained crude product was purified by silica gel column chromatography (ethyl acetate: hexane =1:2) to obtain 0.8 g of the desired product (Intermediate No. 48). The NMR analytical data of this product are as follows.

$^1$H NMR(CDCl$_3$,400Hz): 3.40(3H,s); 3.73(1H,d,J=6.8Hz); 3.89(1H,dd,J =6.8,4.4Hz); 4.07(1H,br,d,J=15Hz); 4.11(1H,dd,J=14.4,1.6Hz); 5.06(1H,t,J =4.4Hz); 5.36(1H,s); 7.20(1H,dt,J=4.4,1.6)

Now, specific Preparation Examples for the compounds of the formula (I) will be described.

PREPARATION EXAMPLE 1

Preparation of 1,6-anhydro-3,4-dideoxy-β-D-threo-hex-3-enopyranose (Compound No. 1)

50 ml of a dry diethyl ether solution containing 20 g of 1,6-anhydro-3,4-dideoxy-β-D-glycero-hex-3-enopyranos-2-ulose, was gradually dropwise added to 500 ml of a dry diethyl ether suspension containing 3.0 g of lithium aluminum hydride, at 0° C. under an inert atmosphere of nitrogen gas. After completion of the dropwise addition, the mixture was immediately returned to room temperature, and stirring was continued for 30 minutes. Disappearance of the starting material was confirmed by thin layer chromatography, and then a small amount of water was added to inactivate an excess amount of lithium aluminum hydride. The mixture was further stirred for 30 minutes, and the reaction mixture was filtered through Celite® to remove the precipitate. The precipitate was washed a few times with diethyl ether, and the washing solutions were concentrated under reduced pressure together with the filtrate. Precipitated crude crystals were recrystallized from diethyl ether to obtain 14.5 g of the desired product (Compound No. 1). The NMR analytical data and physical properties of this product were as follows.

$^1$H NMR(CDCl$_3$,400MHz): 3.73(1H,dd,J=6.4,4.0Hz); 3.82(1H,d,J=6.4Hz); 4.32(1H,br,s); 4.65(1H,t,J=4.0Hz); 5.51(1H,t,J=2.2Hz); 5.69(1H,dt,J=10.0,2.2Hz); 6.09(1H,dd,J=10.0,4.0Hz)

m.p. 69°–71° C.

PREPARATION EXAMPLE 2

Preparation of 1,6-anhydro-3,4-dideoxy-2-O-isovaleryl-β-D-threo-hex-3-enopyranose (Compound No. 2; an isovaleric acid ester of Compound No. 1)

0.7 g of isovaleryl chloride was gradually added to 30 ml of a dry pyridine solution containing 0.5 g of 1,6-anhydro-3,4-dideoxy-β-D-threo-hex-3-enopyranose obtained in the above Preparation Example 1, at 0° C. under an inert atmosphere of nitrogen gas. The mixture was stirred for about 10 minutes. Then, the ice bath was removed, and the mixture was further stirred at room temperature for two hours. To the reaction mixture, a small amount of water was added, and the solvent was distilled off under reduced pressure. The obtained crude product was dissolved in 200 ml of ethyl acetate, and the solution was washed three times with 200 ml of a saturated sodium chloride aqueous solution. The organic layer was dried over anhydrous sodium sulfate, and then the solvent was distilled off under reduced pressure. The obtained syrup crude product was purified by silica gel column chromatography (ethyl acetate: hexane=1:5) to obtain 0.85 g of the desired product (Compound No. 2) as a colorless liquid. The NMR analytical data of this product are as follows.

$^1$H NMR(CDCl$_3$,400MHz): 0.97(6H,d,J=6.9Hz); 2.12(1H,qqt,J=6.9,6.9,6.9Hz); 2.27(2H,d,J=6.9Hz); 3.79(1H,dd,J=6.6,4.0Hz); 3.97(1H,d,J=6.6Hz); 4.68(1H,t,J=4.0Hz); 5.53(1H,br,s); 5.61(1H,dt,J=9.6,2.0Hz); 5.63(1H,m); 6.19(1H,ddd,J=9.6,4.0,1.2Hz)

The following compounds were prepared in the same manner as in the above Preparation Example 2, and their physical properties will be given.

Compound No. 3 (Crotonic acid ester of Compound No. 1)

$^1$H NMR(CDCl$_3$, 400MHz): 1.95(3H,dd,J=6.8,1.6Hz); 3.80(1H,ddd,J=6.5,4.2,1.2Hz); 3.98(1H,d,J=6.5Hz); 4.69(1H,t,J=4.2Hz); 5.55(1H,m); 5.65(1H,dt, J=9.2,2.3Hz); 5.66(1H, m); 5.92(1H,dq,J=15.5,1.6Hz); 6.19(1H,ddt,J=9.2, 4.2.1.2Hz); 7.04(1H,dq,J=15.5,6.8Hz)

Compound No. 4 (Cyclohexanoic acid ester of Compound No. 1)

$^1$H NMR(CDCl$_3$,400MHz): 1.15–1.30(3H,m); 1.43(2H,m); 1.61(1H,m); 1.73(2H, m); 1.90(2H,m); 2.37(1H,tt,J=11.4,3.3Hz); 3.76(1H,ddd,J=6.5,4.1,1.2Hz); 3.94(1H,d,J=6.5Hz); 4.66(1H,t,J=4.1Hz); 5.47(1H,m); 5.58(1H,dt,J=9.7,2.2Hz); 5.60(1H,m); 6.17(1H,ddd,J=9.7,3.7,1.2Hz)

Compound No. 5 (Benzoic acid ester of Compound No. 1)

$^1$H NMR(CDCl$_3$,400MHz): 3.84(1H,ddd,J=6.5,4.2,1.1Hz); 4.03(1H,d,J=6.5Hz); 4.74(1H,t,J=4.2Hz); 5.74(2H,m); 5.78(1H,m); 6.26(1H,dd,J=9.2,4.2Hz); 7.44(2H,t,J=7.5Hz); 7.57(1H,tt,J=7.5,1.5Hz); 8.09(2H,m)
m.p. 116°–117° C.

Compound No. 6 (n-Hexanoic acid ester of Compound No. 1)

$^1$H NMR(CDCl$_3$,400MHz): 0.88(3H,t,J=6.6Hz); 1.32(4H,m); 1.64(2H,m); 2.38(2H,t,J=7.7Hz); 3.80(1H,m); 3.98(1H,d,J=7.1Hz); 4.68(1H,t,J=4.8Hz); 5.52(1H,br,s); 5.61(1H,m); 5.64(1H,br,s); 6.19(1H,dd,J=11.1,4.8Hz)

Compound No. 7 (Palmitic acid ester of Compound No. 1)

$^1$H NMR(CDCl$_3$,400MHz): 0.88(3H,t,J=6.8Hz); 1.25(24H,br,s); 1.60–1.70(2H,m); 2.38(2H,dd,J=7.6,6.8Hz); 3.80(1H,ddd,J=6.4,4.0,1.0Hz); 3.98(1H, d,J=6.4Hz); 4.69(1H,t,J=4.0Hz); 5.52(1H,m); 5.62(1H,dt,J=10.0,2.2Hz); 5.64(1H,m); 6.20(1H,m)
m.p. 39°–41° C.
$[\alpha]^{20}_D = -17.4(c=0.402, \text{chloroform})$

Compound No. 109 (Palmitic acid ester of Compound No. 103)

$^1$H NMR(CDCl$_3$,400MHz): 0.88(3H,t,J=6.8Hz); 1.25(24H,br,s); 1.63(2H, quin,J=7.2Hz); 2.35(1H,t,J=7.2Hz); 3.72(2H,m); 4.76(1H,t,J=4.4Hz); 4.78(1H,br,d,J=4.0Hz); 5.53(1H,m); 5.78(1H,ddd,J=9.6,4.0,2.0Hz); 6.31(1H,ddd, J=9.6,4.4,0.8Hz)

Compound No. 8 (Oleic acid ester of Compound No. 1)

$^1$H NMR(CDCl$_3$,400MHz): 0.90(3H,t,J=7.6Hz); 1.35–1.23(20H,m); 1.64(2H,m); 1.98(4H,m); 2.38(2H,t,J=7.7Hz); 3.79(1H,ddd,J=6.5,4.2,1.5Hz); 3.97 (1H,d,J=6.5Hz); 4.68(1H,t,J=4.2Hz); 5.85(2H,m); 5.52(1H,br,s); 5.62(1H,dt, J=9.9,1.6Hz); 5.63(1H,m); 6.29(1H,dd,J=9.9,4.2Hz)

Compound No. 9 (Acetic acid ester of Compound No. 1)

$^1$H NMR(CDCl$_3$,400MHz): 2.14(3H,s); 3.80(1H,ddd,J=6.8,4.4,0.8Hz); 3.98(1H,d,J=6.8Hz); 4.69(1H,t,J=4.4Hz); 5.52(1H,m); 5.63(1H,m); 5.65(1H,d, J=2.8Hz); 6.20(1H,ddt,J=9.2,4.4,0.8Hz)

Compound No. 10 (α-chloroacetic acid ester of Compound No. 1)

$^1$H NMR(CDCl$_3$, 400MHz): 3.81(1H,ddd,J=6.8,4.0,1.0Hz); 3.97(1H,d,J=6.8Hz); 4.13(1H,d,J=15.2Hz); 4.17(1H,d,J=15.2Hz); 4.71(1H,t,J=4.0Hz); 5.59(1H, m); 5.64(1H,dt,J=10.0,2.2Hz); 5.67(1H,t,J=2.2Hz); 6.25(1H,ddd,J=10.0,4.0,1.0HZ)
$[\alpha]^{20}_D = -43.1(c=0.627, \text{chloroform})$

Compound No. 11 (O-acetylsalicylic acid ester of Compound No. 1)

$^1$H NMR(CDCl$_3$,400MHz): 2.36(3H,s); 3.83(1H,ddd,J=6.8,4.4,1.6Hz); 3.98(1H,d,J=6.8Hz); 4.72(1H,t,J=4.4Hz); 5.72(3H,m); 6.24(1H,ddd,J=10.8,4.4,1.6Hz); 7.10(1H,dd,J=7.6,1.2Hz); 7.31(1H,td,J=7.6,1.2Hz); 7.56(1H,td,J=7.6,1.2Hz); 8.08(1H,dd,J=7.6,1.2Hz)

PREPARATION EXAMPLE 3

Preparation of 1,6-anhydro-2-O-decanoyl-3,4-dideoxy-β-D-threo-hex-3-enopyranose (Compound No. 12; decanoic acid ester of Compound No. 1)

0.6 g of decanoic acid, 0.97 g of dicyclohexylcarbodiimide and 28 mg of N,N-dimethylaminopyridine were added to 50 ml of a dry methylene chloride solution containing 0.3 g of 1,6-anhydro-3,4-dideoxy-β-D-threo-hex-B-enopyranose obtained in the above Preparation Example 1, while stirring under an inert atmosphere of nitrogen gas. The reaction mixture was stirred for 12 hours at room temperature. Then, the formed precipitate was filtered off by Celite ®, and the filtrate was concentrated under reduced pressure. The obtained syrup crude product was purified by silica gel column chromatography (ethyl acetate: hexane=1:3) to obtain 0.38 g of the desired product (Compound No. 12). The NMR analytical data of this product are as follows.

$^1$H NMR(CDCl$_3$,400MHz): 0.87(3H,t,J=6.8Hz); 1.26(12H,m); 1.64(2H, quin., J=7.5Hz); 2.36(1H,dt,J=16.8,7.5Hz); 2.40(1H,dt,J=16.8,7.5Hz); 3.97(1H, ddd,J=6.4,4.0,1.0Hz); 3.98(1H,d,J=6.4Hz);

4.69(1H,t,J=4.0Hz); 5.52(1H,m);
5.63(1H,dt,J=9.6,2.2Hz); 5.65(1H,m);
6.19(1H,ddd,J=9.6,4.0,1.0Hz)

The following compounds were prepared in the same manner as in the above Preparation Example 3, and their physical properties will be given.

Compound No. 13 (6-Bromohexanoic acid ester of Compound No. 1)

$^1$H NMR(CDCl$_3$,400MHz): 1.49(2H,tt,J=8.0,6.8Hz); 1.68(2H,quin. J=8.0Hz); 1.88(2H,quin,J=6.8Hz); 2.41(2H,td,J=8.0,1.6Hz); 3.40(2H,t,J=6.8Hz); 3.79(1H,ddd,J=6.8,4.4,1.6Hz); 3.97(1H,d,J=6.8Hz); 4.69(1H,t,J=4.4Hz); 5.52(1H, m); 5.62(1H,dt,J=10.0,2.0Hz); 5.64(1H,m); 6.20(1H,ddd,J=10.0,4.4,1.6Hz)

Compound No. 14 (2-Thiophenecarboxylic acid ester of Compound No. 1)

$^1$H NMR (CDCl$_3$,400MHz): 3.83(1H,ddd,J=6.8,4.5,1.0Hz); 4.02(1H,d,J=6.8Hz); 4.73(1H,t,J=4.5Hz); 5.69(1H,m); 5.75(1H,dt,J=9.9,2.3Hz); 5.77(1H,m); 6.25(1H,ddd,J=9.9,4.5,1.0Hz); 7.11(1H,dd,J=4.8,3.8Hz); 7.59(1H,dd,J=4.8,0.9Hz); 7.86(1H,dd,J=3.8,0.9Hz)
m.p. 69°–71° C.

Compound No. 15 (Nicotinic acid ester of Compound No. 1)

$^1$H NMR(CDCl$_3$,400MHz): 3.84(1H,ddd,J=6.4,4.4,1.2Hz); 4.02(1H,d,J=6.4Hz); 4.75(1H,t,J=4.4Hz); 5.74(2H,m); 5.77(1H,dt,J=9.6,2.4Hz); 6.29(1H,ddd,J=9.6,4.4,1.2Hz); 7.40(1H,ddd,J=8.0,5.0,1.2Hz); 8.35(1H,dt,J=8.0,1.2Hz); 8.79(1H,dd,J=5.0,1.2Hz); 9.27(1H,br,d,J=1.2Hz)
m.p. 76°–81° C.

Compound No. 16 (p-Chlorobenzoic acid ester of Compound No. 1)

$^1$H NMR(CDCl$_3$, 400MHz): 3.83(1H,ddd,J=6.4,4.0,1.2Hz); 4.02(1H,d,J=6.4Hz); 4.74(1H,t,J=4.0Hz); 5.72(1H,m); 5.74(1H,dt,J=9.2,2.4Hz); 5.76(1H,m); 6.26(1H,ddd,J=9.2,4.0,1.2Hz); 7.41(2H,dt,J=8.8,2.0Hz); 8.02(2H,dt,J=8.8,2.0Hz)
m.p. 57°–59° C.

Compound No. 17 (2-Furancarboxylic acid ester of Compound No. 1)

$^1$H NMR(CDCl$_3$, 400MHz): 3.82(1H,dd,J=6.4,4.4Hz); 4.02(1H,d,J=6.4Hz); 4.72(1H,t,J=4.4Hz); 5.71(1H,m); 5.72(1H,m); 5.75(1H,m); 6.25(1H,dd,J=9.6,4.4Hz); 6.51(1H,dd,J=3.4,2.0Hz); 7.26(1H,dd,J=3.4,1.0Hz); 7.59(1H,m)
m.p. 86°–88° C.

Compound No. 18 (Cinnamic acid ester of Compound No. 1)

$^1$H NMR(CDCl$_3$,400MHz): 3.83(1H,ddd,J=6.8,4.2,1.6Hz); 4.02(1H,d,J=6.8Hz); 4.73(1H,t,J=4.2Hz); 5.66(1H,m); 5.71(1H,dt,J=10.0,2.2Hz); 5.73(1H,m); 6.24(1H,ddd,J=10.0,4.4,1.6Hz); 6.54(1H,d,J=16.0Hz); 7.39(3H,m); 7.53(2H,m); 7.25(1H,d,J=16.0Hz)
m.p. 147°–153° C.

Compound No. 19 (Anthranic acid ester of Compound No. 1)

$^1$H NMR(CDCl$_3$,400MHz): 3.83(1H,ddd,J=6.8,4.2,0.8Hz); 4.02(1H,d,J=6.8Hz); 4.73(1H,t,J=4.2Hz); 5.71(1H,m); 5.75(2H,m); 6.25(1H,ddd,J=10.2,4.2,0.8Hz); 6.66(1H,ddd,J=8.4,6.8,1.6Hz); 6.67(1H,br,d,J=8.4Hz); 7.28(1H,ddd,J=8.4,6.8,1.6Hz); 7.94(1H,dd,J=8.4,1.6Hz)
m.p. 95°–100° C.

Compound No. 20 (Arachidic acid ester of Compound No. 1)

$^1$H NMR(CDCl$_3$,400MHz): 0.88(3H,t,J=7.2Hz); 1.26(32H,br,s); 1.65(2H, m); 2.38(2H,t,J=7.8Hz); 3.80(1H,ddd,J=6.4,4.3,1.0Hz); 3.98(1H,d,J=6.4Hz); 4.69(1H,t,J=4.3Hz); 5.52(1H,m); 5.62(1H,dt,J=9.6,2.2Hz); 5.64(1H,m); 6.19(1H,dddd,J=9.6,4.3,1.2,1.0Hz)

Compound No. 50 (o-Methylbenzoic acid ester of Compound No. 1)

$^1$H NMR(CDCl$_3$,400MHz): 2.61(3H, s); 3.83(1H,m); 4.01(1H,d,J=6.4Hz); 4.73(1H,t,J=4.1Hz); 5.72(1H,m); 5.76(1H,dt,J=9.5,2.2Hz); 5.79(1H,m); 6.25(1H,dd,J=9.5,4.1Hz); 7.24(2H,m); 7.40(1H,td,J=7.4,1.4Hz); 7.97(1H,dd,J=8.3,1.4Hz)

PREPARATION EXAMPLE 4

Preparation of 1,6-anhydro-3,4-dideoxy-2-O-methoxycarbonyl-β-D-threo-hex-3-enopyranose (Compound No. 21; methyl carbonate ester of Compound No. 1)

0.33 g of methyl chlorocarbonate was gradually added to 30 ml of a dry pyridine solution containing 0.3 g of 1,6-anhydro-3,4-dideoxy-β-D-threo-hexo-3-enopyranose under an inert atmosphere of nitrogen gas. The reaction mixture was stirred at room temperature for 12 hours, and 0.33 g of methyl chlorocarbonate was further added thereto. The mixture was stirred for 30 minutes. A small amount of water was added thereto to inactivate methyl chlorocarbonate. Then, the solvent was distilled off under reduced pressure. To the residue, 200 ml of ethyl acetate was added, and the mixture was washed three times with 200 ml of a saturated sodium chloride aqueous solution. The organic layer was dried over anhydrous sodium sulfate. The solvent was distilled off under reduced pressure, and the obtained syrup crude product was purified by silica gel column chromatography (ethyl acetate: hexane=1:3) to obtain 0.33 g of the desired product (Compound No. 21). The NMR analytical data of this product are as follows.

$^1$H NMR(CDCl$_3$,400MHz): 3.80(1H, m); 3.81(3H,s); 3.96(1H,d,J=6.8Hz); 4.70(1H,t,J=4.4Hz); 5.37(1H,m); 5.68(1H,dt,J=10.0,2.0Hz); 5.71(1H,t,J=2.2Hz); 6.23(1H,ddd,J=10.0,4.4,1.2Hz)

The following compounds were prepared in the same manner as in the above Preparation Example 4, and their physical properties will be given.

Compound No. 22 (Phenyl carbonate ester of Compound No. 1)

$^1$H NMR(CDCl$_3$,400MHz): 3.85(1H,ddd,J=6.8,4.3,1.3Hz); 4.02(1H,d,J=6.8Hz); 4.74(1H,t,J=4.31Hz); 5.47(1H,m);

5.77(1H,dt,J=9.3,2.4Hz); 5.79(1H,m); 6.29(1H,ddt,J=9.3,4.3,1.3Hz); 7.20(2H,m); 7.26(1H,m); 7.39(2H,m)

m.p. 98°–99° C.

Compound No. 26 (Phenyl thiocarbonate ester of Compound No. 1)

$^1$NMR(CDCl$_3$,400MHz):
3.86(1H,ddd,J=6.8,4.0,1.0Hz); 4.05(1H,d,J=6.8Hz); 4.76(1H,t,J=4.0Hz); 5.84(1H,dt,J=10.0,2.4Hz); 5.86(1H,m); 6.05(1H, m); 6.31(1H,ddd,J=10.0,4.0,1.0Hz); 7.31(2H,m); 7.30(1H,tt,J=7.6,1.1Hz); 7.42(2H,tt,J=7.6,2.2Hz)

PREPARATION EXAMPLE 5

Preparation of 1,6-anhydro-3,4-dideoxy-2-O-phenylcarbamoyl-β-D-threo-hex-3-enopyranose (Compound No. 23; phenyl carbamic acid ester of Compound No. 1)

0.56 g of phenyl isocyanate was added at room temperature to 30 ml of a dry toluene solution containing 0.3 g of 1,6-anhydro-3,4-dideoxy-β-D-threo-hex-3-enopyranose under an inert atmosphere of nitrogen gas. Further, 0.1 ml of triethylamine was added thereto, and the reaction mixture was refluxed under heating for two hours. Completion of the reaction was confirmed by thin layer chromatography, and then the solvent was immediately distilled off under reduced pressure to obtain a syrup crude product. This crude product was purified by silica gel chromatography (ethyl acetate: hexane=1:3) to obtain 0.5 g of the desired product (Compound No. 23). The NMR analytical data of this product are as follows.

$^1$H NMR(CDCl$_3$,400MHz):
3.83(1H,ddd,J=7.6,5.2,1.9Hz); 3.99(1H,d,J=7.6Hz); 4.73(1H,t,J=5.2Hz); 5.57(1H,m); 5.71(1H,m); 5.73(1H,dt,J=10.0,2.7 Hz); 6.23(1H,ddd,J=10.0,5.2,1.9Hz); 6.83(1H,br,s); 7.08(1H,tt,J=7.6,1.0Hz); 7.32(2H,t,J=7.6Hz); 7.37(2H,d,J=7.6Hz)

m.p. 107°–109° C.

PREPARATION EXAMPLE 6

Preparation of 1,6-anhydro-3,4-dideoxy-2-O-methylthiocarbamoyl-β-D-threo-hex-3-enopyranose (Compound No. 24; methyl thiocarbonate ester of Compound No. 1)

0.4 g of methyl thioisocyanate was added to 30 ml of a dry toluene solution containing 0.35 g of 1,6-anhydro-3,4-dideoxy-β-D-threo-hex-3-enopyranose under an inert atmosphere of nitrogen gas. Then, sodium hydride (60% dispersion in mineral oil, 1.3 equivalent) was gradually added thereto. After confirming the termination of the generation of hydrogen (from 5 to 10 minutes), the stirring was further continued for one hour. Completion of the reaction was confirmed by thin layer chromatography, and then a small amount of water was added to inactivate sodium hydride. Then, the formed precipitate was removed by filtration with Celite ®-anhydrous sodium sulfate. The filtrate was concentrated under reduced pressure, and the obtained syrup crude product was purified by silica gel column chromatography (ethyl acetate: hexane=2:3) to obtain 0.45 g of the desired product (Compound No. 24). The NMR analytical data of this product are as follows.

$^1$H NMR(CDCl$_3$,400MHz): 2.92(0.9H,d,J=4.6Hz); 3.07(2.1H,d,J=4.6Hz); 3.79(1H,m); 3.94(0.7H,d,J=6.5Hz); 3.97(0.3H,d,J=6.5Hz); 4.70(0.7H,t,J=3.7Hz); 4.71(0.3H,t,J=3.7Hz); 5.72(2H,m); 6.19(2H,m); 6.61(0.7H,br,s); 6.79(0.3H,br,s)

The following compound was prepared in the same manner as in the above Preparation Example 6, and its physical properties will be given.

Compound No. 25 (N-tert-butyl carbamate of Compound No. 1)

$^1$H NMR(CDCl$_3$,400MHz): 1.31(9H,s); 3.79(1H,ddd,J=6.4,4.4,1.5Hz); 3.95(1H,d,J=6.4Hz); 4.68(1H,t,J=4.4Hz); 4.87(1H,br,s); 5.41(1H,br,s); 5.65(1H,m); 5.66(1H,dt,J=9.6,2.2Hz); 6.16(1H,ddd,J=9.6,4.4,1.5Hz)

m.p. 113°–115° C.

PREPARATION EXAMPLE 7

Preparation of 1,6-anhydro-3,4-dideoxy-2-C-vinyl-β-D-threo-hex-3-enopyranose (Compound No. 27)

9.5 ml (1 mol) of vinyl magnesium bromide was gradually added to 50 ml of a dry tetrahydrofuran solution containing 1 g of 1,6-anhydro-3,4-dideoxy-β-D-glycero-hex-3-enopyranos-2-ulose under stirring at 0° C. under an inert atmosphere of nitrogen gas. 30 minutes later, the ice bath was removed, and stirring was further continued for 30 minutes at room temperature. Completion of the reaction was confirmed by thin layer chromatography, and then a small amount of water was added to inactivate any excess Grignard reagent. Then, the solvent was distilled off under reduced pressure. The obtained crude product was dissolved in 200 ml of ethyl acetate and washed three times with 200 ml of a saturated sodium chloride aqueous solution. The organic layer was dried over anhydrous sodium sulfate. The solvent was distilled off under reduced pressure, and the obtained syrup product was purified by silica gel column chromatography (ethyl acetate: hexane=1:2) to obtain 0.9 g of the desired product (Compound No. 27). The NMR analytical data of this product are as follows.

$^1$H NMR(CDCl$_3$,400MHz):
3.73(1H,dd,J=6.4,3.9Hz); 3.82(1H,d,J=6.4Hz); 4.68(1H,t,J=3.9Hz); 5.19(1H,br,s); 5.26(1H,dt,J=10.5,1.3Hz); 5.36(1H,dt, J=17.7,1.3Hz); 5.53(1H,dt,J=9.4,1.3Hz); 5.92(1H,ddd,J=17.7,10.5,1.0Hz); 6.09(1H,dd,J=9.4,3.9Hz)

The following compounds were prepared in the same manner as in the above Preparation Example 7, and their physical properties will be given.

Compound No. 28

$^1$H NMR(CDCl$_3$,400MHz): 1.26(3H,s); 3.69(1H,dd,J=7.0,4.6Hz); 3.76(1H, d,J=7.0Hz); 4.62(1H,t,J=4.6Hz); 5.17(1H,d,J=2.2Hz); 5.67(1H,dd,J=10.0,2.2Hz); 5.94(1H,dd,J=10.0,4.6Hz).

Compound No. 29

$^1$H NMR(CDCl$_3$,400MHz): 2.69(1H, s); 3.76(1H,dd,J=6.8,4.4Hz); 3.82(1H, d,J=6.8Hz); 4.73(1H,t,J=4.4Hz); 5.49(1H,d,J=2.0Hz); 5.75(1H,dd,J=9.8,2.0Hz); 6.12(1H,dd,J=9.8,4.4Hz)

m.p. 64°–67° C.

$[\alpha]^{20}_D$= −214.8 (c=0.433, chloroform)

Compound No. 30

$^1$H NMR(CDCl$_3$,400MHz): 0.90(3H,t,J=7.0Hz); 1.35–1.50(4H,m); 1.60–1.75(2H,m); 3.70(1H,dd,J=6.8,4.4Hz); 3.77(1H,d,J=6.8Hz); 4.64(1H,t,J=4.4Hz); 5.22(1H,d,J=2.0Hz); 5.61(1H,dd,J=10.0,2.0Hz); 6.00(1H,dd,J=10.0,4.4Hz)

m.p. 31°–33° C.

Compound No. 31

$^1$H NMR(CDCl$_3$,400MHz): 0.97(3H,t,J=7.2Hz); 1.55(2H,six,J=7.2Hz); 2.23(2H,t,J=7.2Hz); 2.26(1H,br,s); 3.74(1H,dd,J=6.8,4.4Hz); 3.80(1H,d,J=6.8Hz); 4.71(1H,t,J=4.4Hz); 5.44(1H,d,J=2.4Hz); 5.74(1H,dd,J=10.0,2.4Hz); 6.05(1H,dd,J=10.0,4.4Hz)

m.p. 43°–46° C.

PREPARATION EXAMPLE 8

Preparation of 2-O-acetyl-1,6-anhydro-3,4-dideoxy-2-C-methyl-β-D-threo-hex-3-enopyranose (Compound No. 32)

2.4 ml (1.5 mol) of methyl lithium was gradually added to 30 ml of a dry tetrahydrofuran solution containing 0.3 g of 1,6-anhydro-3,4-dideoxy-β-D-glycero-hex-3-enopyranos-2-ulose under starting at 0° C. under an inert atmosphere of nitrogen gas. Completion of the reaction was confirmed by thin layer chromatography, and then 0.25 ml of acetyl chloride was added to the reaction mixture. The ice bath was removed, and the reaction solution was returned to room temperature and further stirred for one hour. The solvent was distilled off under reduced pressure. To the residue, 200 ml of ethyl acetate was added. The mixture was washed three times with 200 ml of a saturated sodium chloride aqueous solution. Then, the organic layer was dried over anhydrous sodium sulfate. The solvent was distilled off under reduced pressure, and the obtained crude product was purified by silica gel column chromatography (ethyl acetate: hexane=1:5) to obtain 0.29 g of the desired product (Compound No. 32). The NMR analytical data of this product are as follows.

$^1$H NMR(CDCl$_3$,400MHz): 1.59(3H,s); 2.05(3H,s); 3.76(1H,dd,J=6.8,4.4Hz); 3.89(1H,d,J=6.8Hz); 4.63(1H,t,J=4.4Hz); 5.78(1H,dd,J=9.6,1.6Hz); 5.89(1H,d,J=1.6Hz); 6.06(1H,dd,J=9.6,4.4Hz)

[α]$^{20}_D$ = −114.7(c=0.654, chloroform)

The following compound was prepared in the same manner as in the above Preparation Example 8, and its physical properties will be given.

Compound No. 33

$^1$H NMR(CDCl$_3$,400MHz): 0.88(3H,t,J=7.2Hz); 1.25(24H,br,s); 1.57(2H, m); 1.59(3H,s); 2.29(2H,td,J=8.0,1.0Hz); 3.76(1H,dd,J=6.4,4.4Hz); 3.87(1H,d,J=6.4Hz); 4.62(1H,t,J=4.4Hz); 5.77(1H,dd,J=9.6,2.0Hz); 5.90(1H,d,J=2.0Hz); 6.06(1H,dd,J=9.6,4.4Hz).

PREPARATION EXAMPLE 9

Preparation of 1,6-anhydro-3,4-dideoxy-β-D-erythro-hex-3-enopyranose (Compound No. 103)

(1) 15 g of p-toluenesulfonyl chloride was added to 50 ml of a dry pyridine solution containing 1,6-anhydro-3,4-dideoxy-β-D-threo-hex-3-enopyranose obtained in the above Preparation Example 1, at room temperature under an inert atmosphere of nitrogen gas. The mixture was stirred for 12 hours, and then a small amount of water was added thereto. Then, the mixture was extracted with 300 ml of toluene. The extract was washed once with 200 ml of 1N hydrochloric acid and then washed three times with 200 ml of a saturated sodium chloride aqueous solution. Then, the organic layer was dried over anhydrous sodium sulfate. The solvent was distilled off under reduced pressure, and then the obtained syrup crude product was purified by silica gel column chromatography (ethyl acetate: hexane=1:1) to obtain 10.5 g of 1,6-anhydro-3,4-dideoxy-2-O-(p-toluene)sulfonyl-β-D-threo-hex-3-enopyranose (Compound No. 46). The NMR analytical data of this product are as follows.

$^1$H NMR(CDCl$_3$,400MHz): 2.45(3H,s); 3.76(1H,ddd,J=6.8,4.0.1.2Hz); 3.94(1H,d,J=6.8Hz); 4.65(1H,t,J=4.0Hz); 5.22(1H,m); 5.45(1H,t,J=2.4Hz); 5.52(1H,dt,J=10.4,2.4Hz); 6.19(1H,ddd,J=10.4,4.0,1.2Hz); 7.35(2H,br,d,J=8.4Hz); 7.83(2H,dt,J=8.4,2.0Hz)

m.p. 81°–83° C.

(2) 10.5 g of 1,6-anhydro-3,4-dideoxy-2-O-(p-toluene)sulfonyl-β-D-threo-hex-3-enopyranose obtained in the above reaction, was dissolved in 100 ml of dried dimethylformamide, and 6 g of sodium benzoate was added thereto. The mixture was refluxed under heating for 30 minutes. The solvent was distilled off under reduced pressure, and 200 ml of water was added to the residue. The mixture was extracted with 300 ml of chloroform. The organic layer was washed once with 200 ml of a saturated sodium hydrogencarbonate aqueous solution and then washed twice with 200 ml of a saturated sodium chloride aqueous solution. Then, the organic layer was dried over anhydrous sodium sulfate. The solvent was distilled off under reduced pressure, and then the obtained syrup crude product was dissolved in 100 ml of dry methanol. Then, 2 ml of a methanol solution of sodium methoxide (28 wt %) was added thereto. The mixture was stirred for 25 minutes at room temperature. The reaction solution was neutralized with a 20% citric acid aqueous solution and then filtered through Celite ® to remove the precipitate. The filtrate was concentrated under reduced pressure, and the obtained crude product was purified by silica gel column chromatography (ethyl acetate: hexane=1:2) to obtain 1.1 g of the desired product (Compound No. 103). The NMR analytical data of this product are as follows.

$^1$H NMR(CDCl$_3$,400MHz): 3.50(1H,br,d,J=3.6Hz); 3.64(2H,m); 4.69(1H,ddd, J=5.0,4.0,1.8Hz); 5.53(1H,t,J=1.8Hz); 5.82(1H,ddd,J=9.6,4.0,1.8Hz); 6.19(1H,ddd,J=9.6,5.0,0.8Hz)

m.p. 50°–54° C.

PREPARATION EXAMPLE 10

Preparation of 1,6-anhydro-3,4-dideoxy-2-O-methyl-β-D-threo-hex-3-enopyranose (Compound No. 41)

0.3 g of 1,6-anhydro-3,4-dideoxy-β-D-threo-hex-3-enoyranose was gradually added to 30 ml of a dry tetrahydrofuran solution of sodium hydride (60% dispersion in mineral oil, 1.3 equivalent) under an inert atmosphere of nitrogen gas. Stirring was continued for 15 minutes, and then 0.45 ml of methyl iodide was added. This reaction solution was stirred at room temperature for 12 hours. A small amount of water was added to inactivate excess sodium hydride, and the reaction solution was concentrated under reduced pressure. To the obtained syrup crude product, 200 ml of ethyl acetate was added, and the mixture was washed three times with 200 ml of a saturated sodium chloride aqueous solution. Then, the mixture was dried over anhydrous sodium sulfate. The solvent was distilled off under reduced pressure, and the obtained syrup product was purified by silica gel column chromatography (ethyl acetate: hexane=2:3) to obtain 0.25 g of the desired product (Compound No. 41). The NMR analytical data of this product are as follows.

$^1$H NMR(CDCl$_3$,400MHz): 3.44(3H,s); 3.74(1H,ddd,J=6.7,4.1,1.3Hz); 3.91(1H,d,J=6.7Hz); 4.07(1H,m); 4.62(1H,t,J=4.1Hz); 5.61(1H,t,J=2.2Hz); 5.72(1H,dt,J=9.8,2.2Hz); 6.09(1H,ddd,J=9.8,4.1,1.3Hz)

The following compounds were prepared in the same manner as in the above Preparation Example 10, and their physical properties will be given.

Compound No. 40 (n-Butyl ether of Compound No. 1)

$^1$H NMR(CDCl$_3$,400MHz): 0.92(3H,t,J=7.2Hz); 1.39(2H,m); 1.60(2H,m); 3.57(1H,dt,J=9.2,6.8Hz); 3.60(1H,dt,J=9.2,6.8Hz); 3.77(1H,ddd,J=6.8.4.0,1.2Hz); 3.97(1H,d,J=6.8Hz); 4.17(1H,m); 4.63(1H,t,J=4.0Hz); 5.62(1H,t,J=2.2Hz); 5.72(1H,dt,J=9.6,2.2Hz); 6.08(1H,ddd,J=9.6,4.0,1.2Hz)

Compound No. 48 (Benzyl ether of Compound No. 1)

$^1$H NMR(CDCl$_3$,400MHz): 3.78(1H,ddd,J=6.4,4.0,1.2Hz); 3.98(1H,d,J=6.4Hz): 4.28(1H,m); 4.63(1H,t,J=4.0Hz); 4.66(1H,d,J=12.0Hz); 4.70(1H,d,J=12.0Hz); 5.56(1H,t,J=2.4Hz); 5.71(1H,dt,J=10.0,2.4Hz); 6.10(1H,ddd,J=10.0,4.0,1.2Hz); 7.29(1H,tt,J=6.8,2.0Hz); 7.34(2H,m); 7.38(2H,m)

PREPARATION EXAMPLE 11

Preparation of 1,6-anhydro-3,4-dideoxy-2-O-(16-hydroxy)hexadecanoyl-$\beta$-D-threo-hex-3-enopyranose (Compound No. 49)

50 ml of a dry tetrahydrofuran solution containing 1 g of 16-hydroxyhexadecanoic acid, 1.1 g of tert-butyldimethylsilyl chloride and 0.75 g of imidazole, was stirred at room temperature for 12 hours under an inert atmosphere of nitrogen gas. The solvent was distilled off under reduced pressure, and then 200 ml of ethyl acetate was added. The mixture was washed three times with 200 ml of a saturated sodium chloride aqueous solution. The organic layer was dried over anhydrous sodium sulfate, and the solvent was distilled off under reduced pressure to obtain a syrup product. Then, 40 ml of diethyl ether, 30 ml of methanol and 30 ml of 1N hydrochloric acid were added thereto, and the mixture was stirred at room temperature for 15 minutes. The solvent was distilled off under reduced pressure, and then 200 ml of ethyl acetate was added. The mixture was washed once with 200 ml of a saturated sodium hydrogencarbonate aqueous solution and then washed twice with 200 ml of a saturated sodium chloride aqueous solution. The organic layer was dried over anhydrous sodium sulfate, and the solvent was distilled off under reduced pressure to obtain a syrup product. This product was purified by silica gel column chromatography (ethyl acetate: hexane =1:1) to obtain 1.4 g of 16-tert-butyldimethylsilyloxyhexadecanoic acid.

A condensation reaction of 16-tert-butyldimethylsilyloxyhexadecanoic acid obtained by the above reaction and Compound No. 1, was conducted in the same manner as in the above Preparation Example 3. Post-treatment was conducted by a conventional method, and then purification was conducted by silica gel column chromatography (ethyl acetate: hexane=1:7). The product was dissolved in 50 ml of dry tetrahydrofuran, and 3 ml of a tetrahydrofuran solution of 1N tetrabutyl ammonium fluoride, was added thereto at room temperature. The mixture was stirred for 12 hours. The solvent was distilled off under reduced pressure, and then 200 ml of ethyl acetate was added. The mixture was washed twice with 200 ml of a saturated sodium chloride aqueous solution and dried over anhydrous sodium sulfate. The solvent was again distilled off under reduced pressure to obtain a syrup product. This product was purified by silica gel column chromatography (ethyl acetate: hexane =2:3) to obtain 0.59 g of the desired product (Compound No. 49). The NMR analytical data of this product are as follows.

$^1$H NMR(CDCl$_3$,400MHz): 1.20-1.37(22H,m); 1.57(2H,quin.,J=7.0Hz); 1.64(2H,quin.,J=7.0Hz); 2.38(2H,t,J=7.4Hz); 2.64(2H,td,J=5.6,5.6Hz); 3.80(1H,ddd,J=6.6,4.1,1.1Hz); 3.98(1H,d,J=6.6Hz); 4.69(1H,t,J=4.1Hz); 5.52(1H, m); 5.62(1H,dt,J=9.5,2.1Hz); 5.64(1H,m); 6.20(1H,ddt,J=9.5,4.1,1.1Hz)

The following compounds were prepared in the same manner as in the above Preparation Example 1 or 2, and their physical properties will be given.

1,6-anhydro-3,4-dideoxy-3-methyl-$\beta$-D-threo-hex-3-enopyranose (Compound No. 51)

$^1$H NMR(CDCl$_3$,400MHz): 1.72(3H,m); 2.03(1H,d,J=12.0Hz); 3.71(1H,dd, J=6.4,4.4Hz); 3.78(1H,d,J=6.4Hz); 4.11(1H,m); 4.60(1H,t,J=4.4Hz); 5.51(1H,d,J=2.8Hz); 5.80(1H,dd,J=4.4,1.6Hz) m.p. 62.5°–64° C.

1,6-anhydro-3,4-dideoxy-3-ethyl-$\beta$-D-threo-hex-3-enopyranose (Compound No. 95)

$^1$H NMR(CDCl$_3$,400MHz): 1.02(3H,t,J=7.2Hz); 1.57(1H,br,s); 2.12(2H,m); 3.73(1H,dd,J=6.0,4.4Hz); 3.78(1H,d,J=6.0Hz); 4.21(1H,d,J=3.2Hz); 4.65(1H,t,J=4.4Hz); 5.53(1H,d,J=3.2Hz); 5.80(1H,m) m.p. 75°–76° C.

1,6-anhydro-3-butyl-3,4-dideoxy-$\beta$-D-threo-hex-3-enopyranose (Compound No. 97)

$^1$H NMR(CDCl$_3$,400MHz): 0.94(3H,t,J=7.2Hz); 1.41(4H,m); 1.65(1H,br,s); 2.06(1H,ddd,J=15.0,9.6,6.0Hz); 2.18(1H,ddd,J=15.0,8.8,5.6Hz); 3.72(1H, dd,J=6.8,4.0Hz); 3.78(1H,d,J=6.8Hz); 4.19(1H,d,J=2.8Hz); 4.63(1H,t,J=4.0Hz); 5.52(1H,d,J=2.8Hz); 5.79(1H,br,d,J=5Hz) m.p. 43°–44° C.

1,6-anhydro-3,4-dideoxy-3-methoxymethyl-$\beta$-D-threo-hex-3-enopyranose (Compound No. 96)

$^1$H NMR(CDCl$_3$,400MHz): 3.35(3H,s); 3.75(1H,dd,J=6.8,4.4Hz); 3.83(1H, d,J=6.8Hz); 3.91(1H,br,d,J=13Hz); 4.01(1H,br,d,J=13Hz); 4.32(1H,br,d,J=2Hz); 4.70(1H,t,J=4.4Hz); 5.53(1H,d,J=2.8Hz); 6.09(1H,m)

m.p. 53°-56° C.

Compound No. 98

¹H NMR(CDCl₃,400MHz): 1.63(3H,s); 3.72(1H,dd,J=5.6,4.4Hz); 3.92(1H,d,J=5.6Hz); 4.61(1H,t,J=4.4Hz); 5.60(1H,br,s); 5.68(1H,d,J=2.4Hz); 5.90(1H,m); 6.46(1H,dd,J=3.6,2.0Hz); 7.21(1H,d,J=3.6Hz); 7.54(1H,s)

Compound No. 99

¹H NMR(CDCl₃,400MHz): 2.85(1H,s); 3.82(1H,dd,J=6.8,4.3Hz); 3.94(1H,d,J=6.8Hz); 4.76(1H,t,J=4.3Hz); 6.01(1H,dd,J=9.7,2.0Hz); 6.18(1H,d,J=2.0Hz); 6.27(1H,dd,J=9.7,4.3Hz); 6.51(1H,dd,J=3.3,1.3Hz); 7.23(1H,d,J=3.3Hz); 7.58(1H,br,s)

Compound No. 100

¹H NMR(CDCl₃,400MHz): 1.57(3H,s); 3.66(1H,dd,J=5.6,4.4Hz); 3.83(1H,d,J=5.6Hz); 4.06(1H,br,s); 4.50(1H,t,J=4.4Hz); 4.54(1H,d,J=13.0Hz); 4.59(1H,d,J=13.0Hz); 5.40(1H,d,J=2.4Hz); 5.72(1H,m); 6.28(1H,dd,J=3.0,2.0Hz); 6.30(1H,d,J=3.0Hz); 7.36(1H,s)

Compound No. 101

¹H NMR(CDCl₃,400MHz): 3.77(1H,ddd,J=7.2,4.4,1.2Hz); 3.96(1H,d,J=7.2Hz); 4.31(1H,m); 4.60(1H,d,J=13.2Hz); 4.63(1H,m); 4.64(1H,d,J=13.2Hz); 5.50(1H,t,J=2.4Hz); 5.64(1H,dt,J=9.6,2.4Hz); 6.09(1H,ddd,J=9.6,4.4,1.2Hz); 6.36(2H,m); 7.41(1H,dd,J=1.6,0.8Hz)

Compound No. 102

¹H NMR(CDCl₃,400MHz): 2.92(1H,s); 3.78(1H,dd,J=6.8,4.4Hz); 3.95(1H,d,J=6.8Hz); 4.17(1H,dt,J=4.4Hz); 4.73(1H,d,J=12.6Hz); 4.80(1H,d,J=12.6Hz); 5.57(1H,d,J=2.0Hz); 5.70(1H,dd,J=9.6,2.0Hz); 6.12(1H,dd,J=9.6,4.4Hz); 6.33(2H,m); 7.41(1H,m)

Now, enopyranose derivatives of the formula (I-1) or (I-2) will be presented in Tables 3 to 11.

TABLE 3

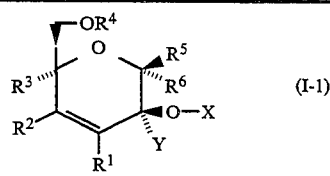

(I-1)

| Compound No. | R¹ | R² | R³ | R⁴ R⁵ | R⁶ | X | Y |
|---|---|---|---|---|---|---|---|
| 1 | H | H | H | Single bond | H | H | H |
| 2 | H | H | H | Single bond | H | —COCH₂CH(CH₃)₂ | H |
| 3 | H | H | H | Single bond | H | —COCH=CHCH₃ | H |
| 4 | H | H | H | Single bond | H | —CO—⟨cyclohexyl⟩ | H |
| 5 | H | H | H | Single bond | H | —CO—⟨phenyl⟩ | H |
| 6 | H | H | H | Single bond | H | —CO(CH₂)₄CH₃ | H |
| 7 | H | H | H | Single bond | H | —CO(CH₂)₁₄CH₃ | H |
| 8 | H | H | H | Single bond | H | —CO(CH₂)₇CH=CH(CH₂)₇CH₃ | H |
| 9 | H | H | H | Single bond | H | —COCH₃ | H |
| 10 | H | H | H | Single bond | H | —COCH₂Cl | H |
| 11 | H | H | H | Single bond | H | —CO—⟨phenyl-OCOCH₃⟩ | H |
| 12 | H | H | H | Single bond | H | —CO(CH₂)₈CH₃ | H |

TABLE 4

| Compound No. | R¹ | R² | R³ | R⁴ R⁵ | R⁶ | X | Y |
|---|---|---|---|---|---|---|---|
| 13 | H | H | H | Single bond | H | —CO(CH₂)₅Br | H |
| 14 | H | H | H | Single bond | H | —CO—⟨thiophene⟩ | H |

TABLE 4-continued

| Compound No. | R¹ | R² | R³ | R⁴ R⁵ | R⁶ | X | Y |
|---|---|---|---|---|---|---|---|
| 15 | H | H | H | Single bond | H | 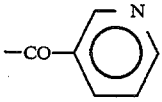 | H |
| 16 | H | H | H | Single bond | H | 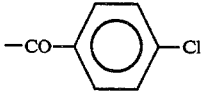 | H |
| 17 | H | H | H | Single bond | H |  | H |
| 18 | H | H | H | Single bond | H | 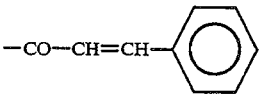 | H |
| 19 | H | H | H | Single bond | H | 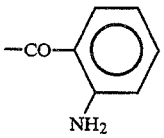 | H |
| 20 | H | H | H | Single bond | H | —CO(CH$_2$)$_{18}$CH$_3$ | H |
| 21 | H | H | H | Single bond | H | —COOCH$_3$ | H |
| 22 | H | H | H | Single bond | H | 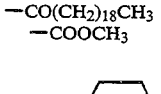 | H |
| 23 | H | H | H | Single bond | H | 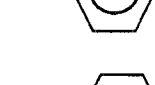 | H |
| 24 | H | H | H | Single bond | H | —CSNHCH$_3$ | H |
| 25 | H | H | H | Single bond | H | —CONHC(CH$_3$)$_3$ | H |
| 26 | H | H | H | Single bond | H |  | H |

TABLE 5

| Compound No. | R¹ | R² | R³ | R⁴ R⁵ | R⁶ | X | Y |
|---|---|---|---|---|---|---|---|
| 27 | H | H | H | Single bond | H | H | —CH=CH$_2$ |
| 28 | H | H | H | Single bond | H | H | —CH$_3$ |
| 29 | H | H | H | Single bond | H | H | —C≡CH |
| 30 | H | H | H | Single bond | H | H | —(CH$_2$)$_3$CH$_3$ |
| 31 | H | H | H | Single bond | H | H | —C≡CCH$_2$CH$_2$CH$_3$ |
| 32 | H | H | H | Single bond | H | —COCH$_3$ | —CH$_3$ |
| 33 | H | H | H | Single bond | H | —CO(CH$_2$)$_{14}$CH$_3$ | —CH$_3$ |
| 34 | H | H | H | Single bond | H | —CHO | H |
| 35 | H | H | H | Single bond | H | H | —CH$_2$OH |

TABLE 5-continued

| Compound No. | R¹ | R² | R³ | R⁴ R⁵ | R⁶ | X | Y |
|---|---|---|---|---|---|---|---|
| 36 | H | H | H | Single bond | H | H | —CH₂NH₂ |
| 37 | H | H | H | Single bond | H | H | —CH₂OCOCH₃ |
| 38 | H | H | H | Single bond | H | H | —(CH₂)₉CH₃ |
| 39 | H | H | H | Single bond | H | H | —(CH₂)₁₇CH₃ |
| 40 | H | H | H | Single bond | H | —(CH₂)₃CH₃ | H |

TABLE 6

| Compound No. | R¹ | R² | R³ | R⁴ R⁵ | R⁶ | X | Y |
|---|---|---|---|---|---|---|---|
| 41 | H | H | H | Single bond | H | CH₃ | H |
| 42 | H | H | H | Single bond | H | H | —CH₂N₃ |
| 43 | H | H | H | Single bond | H | H | —CH₂-(2-methylphenyl) 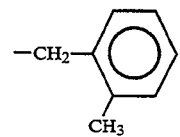 |
| 44 | H | H | H | Single bond | H | —CO-(2,4-dinitrophenyl) 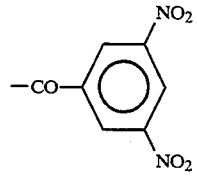 | H |
| 45 | H | H | H | Single bond | H | —SO₂CH₃ | H |
| 46 | H | H | H | Single bond | H | —SO₂-(4-methylphenyl) 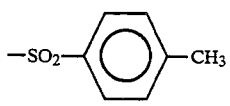 | H |
| 47 | H | H | H | Single bond | H | H | —CH₂NH₂·HCl |
| 48 | H | H | H | Single bond | H | —CH₂-phenyl | H |
| 49 | H | H | H | Single bond | H | —CO(CH₂)₁₄CH₂OH | H |
| 50 | H | H | H | Single bond | H | —CO-(2-methylphenyl) 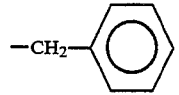 | H |
| 51 | CH₃ | H | H | Single bond | H | H | H |
| 52 | —OSO₂-(4-methylphenyl) 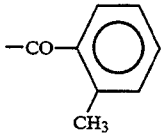 | H | H | Single bond | H | H | H |
| 53 | Br | H | H | Single bond | H | H | H |
| 54 | I | H | H | Single bond | H | H | H |

TABLE 7

| Compound No. | R¹ | R² | R³ | R⁴ | R⁵ | R⁶ | X | Y |
|---|---|---|---|---|---|---|---|---|
| 55 | —OCOCH₃ | H | H | Single bond | | H | H | H |

TABLE 7-continued

| Compound No. | R¹ | R² | R³ | R⁴ | R⁵ | R⁶ | X | Y |
|---|---|---|---|---|---|---|---|---|
| 56 | H | H | H | Single bond | | —CH₂OH | H | H |
| 57 | H | H | H | Single bond | | CH₃ | H | H |
| 58 | 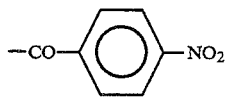 | H | H | Single bond | | H | H | H |
| 59 | H | H | H | H | H/OH | OH/H | H | H |
| 60 | H | H | H | H | H | —OCH₃ | H | H |
| 61 | H | H | H | —COCH₃ | H | —OCH₃ | H | H |
| 62 | H | H | H | SitBuMe₂ | H | —OCH₃ | H | H |
| 63 | H | H | H | H | —OCH₃ | H | H | H |
| 64 | H | H | H | —COCH₃ | H | —OCOCH₃ | H | H |
| 65 | Br | H | H | —COCH₃ | H | —OCOCH₃ | H | H |
| 66 | H | H | H | —COCH₃ | H/OH | OH/H | H | H |
| 67 | Br | H | H | —COCH₃ | H/OH | OH/H | H | H |
| 68 | H | H | H | —COC₂H₅ | H | —OCOC₂H₅ | H | H |
| 69 | CH₃ | H | H | H | H | —OCH₃ | H | H |
| 70 | H | H | H | CH₃ | —OCH₃ | H | H | H |
| 71 | H | H | H | 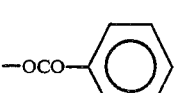 | —OCH₃ | H | H | H |
| 72 | H | H | H | Tr | H | —OCH₃ | H | H |
| 73 | H | H | H | —COCH₃ | —OC₄H₉t | H | H | H |
| 74 | H | H | H | H | —OC₄H₉t | H | H | H |
| 75 | H | H | H | —COCH₃ | —OC₃H₇i | H | H | H |

TABLE 8

| Compound No. | R¹ | R² | R³ | R⁴ | R⁵ | R⁶ | X | Y |
|---|---|---|---|---|---|---|---|---|
| 76 | H | H | H | CH₃ | H/OH | OH/H | H | H |
| 77 | H | H | H | SitBuMe₂ | OC₂H₅ | H | H | H |
| 78 | H | H | H | SitBuMe₂ | OC₄H₉t | H | H | H |
| 79 | H | H | H | 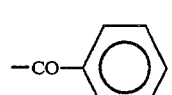 | OCH₃ | H | H | H |
| 80 | H | H | H | —CH(CH₃)OC₂H₅ | OCH₃ | H | H | H |
| 81 | —NHCOCH₃ | H | H | —COCH₃ | OCH₃ | H | H | H |
| 82 | —OCOCH₃ | H | H | —COCH₃ | OCH₃ | H | H | H |
| 83 | 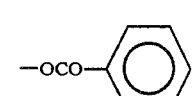 | H | Br | 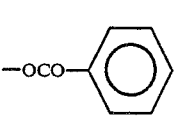 | | 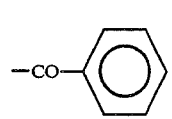 | H | H |
| 84 | 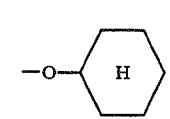 | H | H | 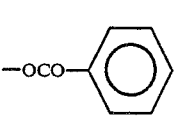 | |  | H | H |
| 85 | —OCOC₄H₉t | H | H | —COC₄H₉t | —OCH₃ | H | H | H |
| 86 |  | H | H | H | —OCH₃ | H | H | H |

TABLE 8-continued

| Compound No. | R¹ | R² | R³ | R⁴ | R⁵ | R⁶ | X | Y |
|---|---|---|---|---|---|---|---|---|
| 87 | —OCH₃ | H | H | CH₃ | 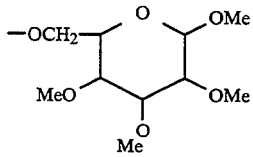 | H | H | H |
| 88 | —OCOCH₃ | H | H | —COCH₃ | —OCOCH₃ | H | H | H |
| 89 | H | CH₃ | H | 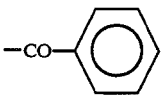 | —OC₂H₅ | H | H | H |
| 90 | H | CH₃ | H | Tr | —OC₂H₅ | H | H | H |
| 91 | 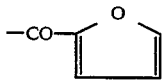 | H | H | Single bond | | H | H | H |
| 92 | H | CH₃ | H | | Single bond | H | H | H |
| 93 | —CH=CH₂ | H | H | | Single bond | H | H | H |
| 94 | —C≡CH | H | H | | Single bond | H | H | H |

TABLE 9

| Compound No. | R¹ | R² | R³ | R⁴ R⁵ | R⁶ | X | Y |
|---|---|---|---|---|---|---|---|
| 95 | —CH₂OCH₃ | H | H | Single bond | H | H | H |
| 96 | —C₂H₅ | H | H | Single bond | H | H | H |
| 97 | —(CH₂)₃CH₃ | H | H | Single bond | H | H | H |
| 98 | —CH₃ | H | H | Single bond | H | 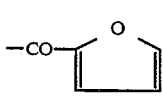 | H |
| 99 | H | H | H | Single bond | H | 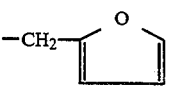 | —CH≡CH |
| 100 | —CH₃ | H | H | Single bond | H | 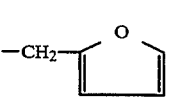 | H |
| 101 | H | H | H | Single bond | H | 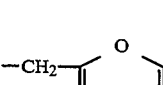 | H |
| 102 | H | H | H | Single bond | H | —CH₂—[furan] | —CH≡CH |

H/OH and OH/H for R⁵ and R⁶ mean that either R⁵ or R⁶ is an OH group.

SitBuMe₂ represents a tert-butyl dimethylsilyl group, C₄H₉t represents a tert-butyl group, and C₃H₇i represents an iso-propyl group.

Tr represents a triphenylmethyl group, and  represents a cyclohexyl group.

TABLE 10

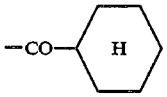

| Compound No. | R¹ | R² | R³ | R⁴ R⁵ | R⁶ | X | Y |
|---|---|---|---|---|---|---|---|
| 103 | H | H | H | Single bond | H | H | H |
| 104 | H | H | H | Single bond | H | —COCH$_2$CH(CH$_3$)$_2$ | H |
| 105 | H | H | H | Single bond | H | —COCH=CHCH$_3$ | H |
| 106 | H | H | H | Single bond | H | 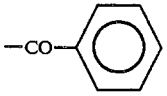 | H |
| 107 | H | H | H | Single bond | H | 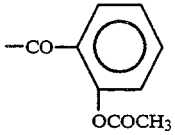 | H |
| 108 | H | H | H | Single bond | H | —CO(CH$_2$)$_4$CH$_3$ | H |
| 109 | H | H | H | Single bond | H | —CO(CH$_2$)$_{14}$CH$_3$ | H |
| 110 | H | H | H | Single bond | H | —CO(CH$_2$)$_7$CH=CH(CH$_2$)$_7$CH$_3$ | H |
| 111 | H | H | H | Single bond | H | —COCH$_3$ | H |
| 112 | H | H | H | Single bond | H | —COCH$_2$Cl | H |
| 113 | H | H | H | Single bond | H | 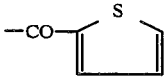 | H |
| 114 | H | H | H | Single bond | H | —CO(CH$_2$)$_8$CH$_3$ | H |

TABLE 11

| Compound No. | R¹ | R² | R³ | R⁴ R⁵ | R⁶ | X | Y |
|---|---|---|---|---|---|---|---|
| 115 | H | H | H | Single bond | H | —CO(CH$_2$)$_5$Br | H |
| 116 | H | H | H | Single bond | H | 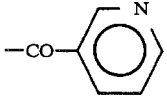 | H |
| 117 | H | H | H | Single bond | H | 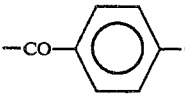 | H |
| 118 | H | H | H | Single bond | H | 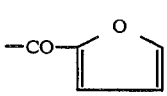 | H |
| 119 | H | H | H | Single bond | H | 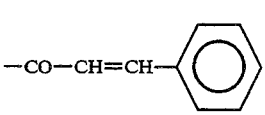 | H |
| 120 | H | H | H | Single bond | H | —CO—CH=CH—⌬ | H |

TABLE 11-continued

| Compound No. | R¹ | R² | R³ | R⁴ R⁵ | R⁶ | X | Y |
|---|---|---|---|---|---|---|---|
| 121 | H | H | H | Single bond | H | 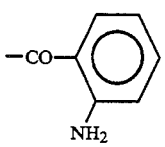 —CO—⟨C₆H₄⟩—NH₂ | H |
| 122 | H | H | H | Single bond | H | —CO(CH₂)₁₈CH₃ | H |
| 123 | H | H | H | Single bond | H | —COOCH₃ | H |
| 124 | H | H | H | Single bond | H | 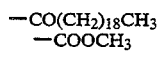 —COO—⟨C₆H₅⟩ | H |
| 125 | H | H | H | Single bond | H | 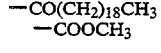 —CONH—⟨C₆H₅⟩ | H |
| 126 | H | H | H | Single bond | H | —CSNHCH₃ | H |
| 127 | H | H | H | Single bond | H | —CONHC(CH₃)₃ | H |
| 128 | H | H | H | Single bond | H | 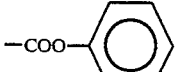 —C(S)O—⟨C₆H₅⟩ | H |

Now, pharmacological tests will be given which show that the enopyranose derivative of the above formula (I) or its salt is useful as an effective component for an immuno-suppressive agent.

Pharmacological Tests (1) Inhibiting effects on collagen-induced arthritis model Male DBA/IJNCrj mice of from 4 to 6 weeks old were used in groups each consisting of four mice. An emulsion of bovine collagen type II (Product No. K41, manufactured by Collagen Gijutsu-Kenshukai) (3 mg/ml) in the same amount by volume of complete Freund's adjuvant (Product No. 642851, manufactured by ICN Immunobiologicals) was injected intradermally at the base of the tail of each mouse (150 μg/0.1 ml/mouse) to induce collagen-induced arthritis. The degree of arthritis was evaluated under the following standards and represented by scores (from 0 to 3 points per foot, the maximum of 12 points as the total score of four feet):

0 Point: No change
1 Point: Detectable swelling in one or more digital joints
2 Points: Mild swelling in one more joints
3 Points: Severe swelling of the entire paw and/or ankylosis For the basic procedure of the above test, reference was made to the Journal of Immunology, Vol. 140, 1477–1484, (1988).

(a) Inhibiting effects on collagen-induced arthritis model

From the 18th day after inoculation of the antigen, administration of the compound of the formula (I) (50 mg/kg) was started. Administration was conducted continuously for four weeks intraperitoneally or orally once a day, whereby the state of arthritis was observed. As a control, saline was used, and the test was conducted in the same manner. The results are shown in FIG. 1.

(2) Effects on various cultured cells (a) Effects on the mitogenic response by murine thymocytes Using BALB/c murine thymocytes, the effect of the compound of the formula (I) on the mitogenic response of lymphocytes to the stimulation by concanavalin A (hereinafter referred to simply as Con A, Product No. L-1000, manufactured by Vector Laboratories) was studied. Namely, $4 \times 10^5$ murine thymocytes were cultured for 48 hours on a microplate with 96 wells in a RPMI1640 solution containing 10% of a fetal bovine serum (hereinafter referred to simply as a 10% FCS-RPMI solution) together with Con A (5 μg/ml) and the compound of the formula (I) (in an incubator, 5% $CO_2$, at 37° C.). Then, 0.5 μCi of $^3$H-thymidine (hereinafter referred to simply as $^3$H-TdR) was added thereto, and the mixture was further cultured for 4 hours. Then, cells were collected by a cell harvester, and the radioactivity (dpm) of $^3$H-TdR uptaken into cells was measured. Such measured amounts of $^3$H-TdR uptaken into the cells were used as indices of the mitogenic response of the murine thymocytes, and the radioactivity at each concentration (from 0.001 to 1,000 μg/ml) of the compound of the formula (I) was compared with the control value treated solely by Con A, to calculate $IC_{50}$ value. The results are shown in Tables 12 and 13. In these Tables 12 and 13, the results of murine thymocytes are shown by (a).

For the basic procedure of this test, reference was made to Selected methods in cellular immunology, p. 144–146 (translated by Katsuyuki Imai et al., published by Rikogakusha, (1982)).

(b) Effects on the murine mixed lymphocyte reaction

Using spleen cells of BALB/c and C57BL/6 mice, the effect of the compound of the formula (I) on the murine mixed lymphocyte reaction in both sides, was studied. Namely, spleen cells of both types of mice were mixed in an equal amount of $5 \times 10^5$ cells each, and the mixed cells were cultured together with the compound of the formula (I) for 48 hours on a microplate with 96 wells by a 10% FCS-RPMI solution (in an incubator, 5% $CO_2$, at 37° C.). Then, 0.5 μCi of $^3$H-TdR was added thereto, and the mixture was further cultured for from 16 to 18 hours. Then, cells were collected by a cell harvester, and the radioactivity (dpm) of $^3$H-TdR uptaken into the cells, was measured. Such measured amounts of $^3$H-TdR uptaken into the cells were used as indices for the mixed lymphocyte reaction, and the radioactivity at each concentration (from 0.001 to 1,000 μg/ml) of the compound of the formula (I) was compared with the non-treated control value, to calculate the $Ic_{50}$ value. The results are shown in Tables 12 and 13. In these Tables 12 and 13, the results of the mixed lymphocyte reaction are shown by (b).

For the basic procedure for this test, reference was made to Selected methods in cellular immunology, p. 147–149 (translated by Katsuyuki Imai et al., published by Rikogakusha, (1982)).

(c) Effects on the murine bone mallow cells

Bone mallow cells were removed from the femur of a BALB/c mouse and suspended in a 10% FCS-RPMI solution. The cell suspension was put into a plastic Petri dish having a diameter of 10 cm and left to stand still (in an incubator, 5% $CO_2$, at 37° C.). Two hours later, only floating cells were recovered, and adhesion cells were removed. $1 \times 10^5$ floating cells were cultured for 48 hours together with a 20% culture supernatant of L929 fibroblastoma and the compound of the formula (I) on a microplate with 96 wells by a 10% FCS-RPMI solution (in an incubator, 5% $CO_2$, at 37° C.). Then, 0.5 μCi of $^3$H-TdR was added thereto, and the mixture was further cultured for 4 hours. Then, cells were collected by a cell harvester, and the radioactivity (dpm) of $^3$H-TdR uptaken into the cells, was measured. Such measured amounts of $^3$H-TdR uptaken into the cells were used as indices for the proliferation of bone mallow cells, and the radioactivity at each concentration (from 0.001 to 1,000 μg/ml) of the compound of the formula (I) was compared with the control value where the L929 culture supernatant was added alone, to calculate the $IC_{50}$ value. The results are shown in Tables 12 and 13. In these Tables 12 and 13, the results of the bone mallow cells are shown by (c).

For the basic procedure of this test, reference was made to Seikagakujikken Koza compiled by Japan Biochemistry Association, Vol. 5, p. 266–270 (published by Tokyo Kagaku Dojin in 1986).

TABLE 12

| Compound No. | $IC_{50}$ value (μg/ml) | | |
|---|---|---|---|
| | a | b | c |
| 1 | 15 | 11 | 69 |
| 2 | 350 | 560 | >1000 |
| 3 | 0.0044 | 0.0044 | 130 |
| 4 | 450 | 140 | 160 |
| 5 | 130 | 130 | 150 |
| 6 | 250 | 540 | 270 |
| 7 | 49 | 76 | 89 |
| 10 | 1.4 | 18 | 68 |

TABLE 12-continued

| Compound No. | $IC_{50}$ value (μg/ml) | | |
|---|---|---|---|
| | a | b | c |
| 11 | 110 | 170 | 210 |
| 12 | 110 | 560 | 560 |
| 13 | 33 | 190 | 330 |
| 14 | 42 | 13 | 500 |
| 15 | 130 | 480 | 310 |
| 16 | 91 | 190 | 170 |
| 17 | 190 | 270 | 510 |
| 19 | 0.39 | >1000 | 160 |
| 20 | 150 | 240 | 400 |
| 22 | 300 | 130 | >1000 |
| 23 | 95 | 170 | 49 |
| 24 | 170 | 100 | 620 |
| 25 | 0.32 | 430 | 340 |
| 26 | 44 | 20 | 200 |

TABLE 13

| Compound No. | $IC_{50}$ value (μg/ml) | | |
|---|---|---|---|
| | a | b | c |
| 27 | 49 | 180 | 44 |
| 28 | 76 | 280 | 150 |
| 29 | 35 | >1000 | >1000 |
| 30 | 110 | 540 | 190 |
| 31 | 180 | 560 | 520 |
| 32 | 320 | 540 | 540 |
| 40 | 160 | >1000 | >1000 |
| 46 | 110 | 22 | 190 |
| 48 | 120 | >1000 | 430 |
| 49 | 11 | 32 | 41 |
| 50 | 52 | 180 | 380 |
| 103 | 780 | >1000 | >1000 |
| 109 | 550 | 740 | >1000 |

(d) Effects on the antibody production from murine spleen cells

Using murine spleen B cells, the effects of the compound of the formula (I) on the IgG1, IgM and IgE antibody production induced by the stimulation by LPS (lipopolysaccharide; Product No. 520.02051, manufactured by Wako Junyaku) and IL4 (interleukin 4), were studied. Namely, spleen cells of a BALB/c mouse were treated with a murine anti-Thy-1 antibody (obtained from Chiba University) and a rabbit complement (Product No. 3051, manufactured by cedarlane) to remove T cells, and $3 \times 10^5$ spleen B cells were cultured for 7 days together with 10 μg/ml of LPS, 100 U/ml of mouse-recombinant IL4 (Product No. MIL-4C, manufactured by Genzyme) and each concentration (from 0.001 to 1,000 μm/ml) of the compound of the formula (I) on a microplate with 96 wells by a 10% FCS-RPMI solution (in an incubator, 5% $CO_2$, at 37° C.).

For the basic procedure of this test, reference was made to The Journal of Immunology, Vol. 136, p. 4538, (1986).

The amount of each antibody in the cell culture supernatant hereby obtained, was measured by the following enzyme-immunoassay. Firstly, on a microplate with 96 wells, 1 μg/ml of a rabbit anti-mouse IgG1 antibody (Product No. 36243, manufactured by Cappel), 1 μg/ml of a goat anti-mouse IgM antibody (Product No. 0611-0201, manufactured by Cappel) or 10 μg/ml of a rat anti-mouse IgE monoclonal antibody (Product No. LO-ME-2, manufactured by Experimental Immunology) was coated (50 μl/well, at room temperature for 60 minutes), and then a nonspecific bond was blocked by a 0.1% bovine serum albumin-containing 10 mM sodium phosphate buffer (pH 7.2) (at room temperature for 60 minutes). Then, the above-mentioned cell culture supernatant or its diluted solution was added in an amount of 50 µl/well and reacted at room temperature for 60 minutes. Further, an alkaline phosphatase-labeled rabbit anti-mouse IgGl antibody (Product No. 61-0122, manufactured by Zymet) diluted 1,000 times, an alkaline phosphatase-labeled rabbit anti-mouse IgM antibody (Product No. 61-6822, manufactured by Zymet) diluted 2,000 times, or an alkaline phosphatase-labeled goat anti-mouse IgE antibody (Product No. PA-284, manufactured by Binding Site) diluted 500 times was added in an amount of 50 µl/well and reacted at room temperature for 60 minutes. 100 µl/well of a 10% diethanol amine buffer solution (pH 9.8) containing p-nitrophenyl phosphate as an enzyme substrate, was reacted, and the absorbance at 405 nm was measured. The amount of each antibody was calculated from the calibration curve of each standard antibody, and the $IC_{50}$ value of the compound of the formula (I) on the antibody production was calculated using as the control value a value obtained in the absence of the compound of the formula (I). The results are shown in Tables 14 and 15 together with the above-mentioned results of the effect on the murine bone mallow cells. In these Tables 14 and 15, the $IC_{50}$ value of the effect on the antibody production was shown by each antibody i.e. IgGl, IgM or IgE, and the above-mentioned results of the murine bone mallow cells are shown by (c).

TABLE 14

| Compound No. | $IC_{50}$ value (µg/ml) | | | |
|---|---|---|---|---|
| | I g Gl | I g M | I g E | c |
| 1 | 37 | 25 | 32 | 69 |
| 2 | 300 | 250 | 370 | >1000 |
| 3 | 2.4 | <0.001 | 0.024 | 130 |
| 4 | 100 | 56 | 11 | 160 |
| 5 | 300 | 170 | 71 | 150 |
| 6 | 450 | 330 | 210 | 270 |
| 7 | 330 | 410 | 180 | 89 |
| 8 | 810 | 340 | 310 | >1000 |
| 9 | 790 | 720 | 320 | >1000 |
| 10 | <0.001 | <0.001 | <0.001 | 68 |
| 11 | 16 | 28 | 32 | 210 |
| 12 | 24 | 0.11 | 28 | 560 |
| 13 | <0.001 | <0.001 | 0.32 | 330 |
| 14 | 10 | 0.89 | 3.7 | 500 |
| 15 | 220 | 78 | 320 | 310 |
| 16 | 41 | 20 | 50 | 170 |
| 17 | 1.0 | 100 | 3.2 | 510 |
| 18 | <0.001 | 0.68 | <0.001 | 370 |
| 19 | 24 | 76 | 32 | 160 |
| 20 | 5.2 | 500 | 3.2 | 400 |
| 21 | 500 | 130 | 17 | >1000 |
| 22 | 670 | 230 | 4.0 | >1000 |

TABLE 15

| Compound No. | $IC_{50}$ value (µg/ml) | | | |
|---|---|---|---|---|
| | I g Gl | I g M | I g E | c |
| 23 | 72 | 69 | 43 | 49 |
| 24 | 17 | 10 | 0.22 | 620 |
| 25 | 0.0015 | 78 | 0.0034 | 340 |
| 26 | 23 | 110 | 4.5 | 200 |
| 27 | 34 | 36 | 24 | 44 |
| 28 | 380 | 590 | 280 | 150 |
| 29 | 380 | >1000 | 320 | >1000 |
| 30 | 190 | 150 | 24 | 190 |
| 31 | 1.5 | 10 | 140 | 520 |
| 32 | 400 | 350 | 2.8 | 540 |
| 33 | 340 | 5.6 | 460 | >1000 |
| 40 | 0.067 | 110 | 0.0026 | >1000 |
| 41 | 670 | >1000 | 0.95 | >1000 |
| 46 | 0.25 | 0.35 | 0.32 | 190 |
| 48 | 34 | 35 | 41 | 430 |
| 49 | <0.1 | 0.43 | <0.1 | 41 |

TABLE 15-continued

| Compound No. | $IC_{50}$ value (µg/ml) | | | |
|---|---|---|---|---|
| | I g Gl | I g M | I g E | c |
| 50 | <0.001 | <0.001 | <0.001 | 380 |
| 103 | 0.45 | 1.3 | 2.1 | >1000 |
| 109 | <0.1 | 31 | <0.1 | >1000 |

TABLE 16

Carrageenan-induced acute inflammation in rats

| Compound No. | Dose (mg/Kg) | Number of rats tested | Swelling of paw ($\times 10^{-2}$ cm$^3$) | |
|---|---|---|---|---|
| | | | Average ± SD | P < |
| Control group | — | 4 | 144 ± 8 | |
| 29 | 50 | 4 | 97 ± 22 | 0.01 |
| 1 | 50 | 4 | 100 ± 33 | 0.05 |
| 17 | 50 | 4 | 95 ± 26 | 0.05 |

Toxicity test

Male DBA1/J mice of 6 weeks old were used in groups each consisting of four mice. The compound of the formula (I) (50 mg/kg) was administered every day for 4 weeks intraperitonially or orally once a day, whereby the change in the body weight and the mortality were examined. As a result, there was no remarkable change in the body weight, and there was no case of death. Thus, the $LD_{50}$ value of the compound of the above formula (I) is 50 mg/kg at the minimum.

The enopyranose derivative of the formula (I) or its salt has an anti-inflammatory activity, and a test example for the anti-inflammatory activity will be given below.

Test for anti-inflammatory activity

A test for an anti-inflammatory activity was conducted by means of carrageenan-induced paw edema model which is commonly used for evaluation of the effectiveness of a common anti-inflammatory agent (NSAID).

0.1 ml of a 1% λ-carrageenan solution was injected intradermally at the sole of the right paw of a SD male rat (six weeks old). Three hours later, the sole volumes of paws on both sides were measured, and the difference in the volume between the right paw and the left paw was taken as the degree of edema. The test compound was orally administered in an amount of 1 ml/100 g (body weight) one hour prior to the administration of carrageenan. To the control group, a physiological saline was administered in the same amount. The results are shown in Table 16.

As is apparent from Table 16, the test compounds showed statistically significant suppressing effects against carrageenan-induced paw edema, whereby the effectiveness as anti-inflammatory agents was confirmed.

When the enopyranose derivative of the formula (I) or its salt is to be used as an effective component of an immuno-suppressive agent, it is administered orally or non-orally usually at a dose of from about 50 mg to 5,000 mg per day for an adult, although the dose may vary depending upon the conditions for administration, etc. The administration of the drug can be conducted per orally, intravenously, intramuscularly, intradermally or permucassaly. Formulations for administration include, for example, powders, microgranules, granules, tablets, pills, capsules, injection solutions, nose drops, suspensions, intravenous drips, ointments, syrups and gradually releasing agents. These formulations can be prepared by conventional methods by using pharmaceutically acceptable common carriers in the same manner as for usual drug formulations.

The present invention provides an immuno-suppressive agent containing a compound of the formula (I) as an effective component. More specifically, the immuno-suppressive agent of the present invention is effective for treatment of a disease caused by abnormal sthenia of an immunological function, for example, an autoimmune disease such as rheumatoid arthritis, systemic lumpus erythematosus, chronic nephritis, chronic thyroiditis or autoimmune hemolytic anemia as well as for suppressing a rejection at the time of transplantation of an organ. Further, it is effective for treatment of an allergy disease or an inflammatory disease, particularly for treatment of an autoimmune disease such as rheumatoid arthritis.

We claim:

1. An immuno-suppressive or anti-inflammatory pharmaceutical composition comprising a therapeutically effective amount of an enopyranose derivative of formula (I) or its pharmaceutically acceptable salt:

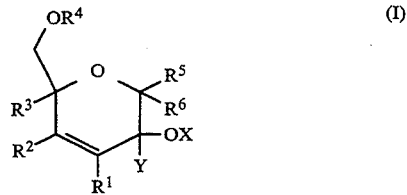

wherein $R^1$ is (a) a hydrogen atom, (b) $C_1$-$C_{20}$ alkyl which may be substituted by one or more members selected from the group consisting of $C_1$-$C_{20}$ alkoxy, phenyl and hydroxyl, (c) $C_2$-$C_{20}$ alkenyl, (d) $C_2$-$C_{20}$ alkynyl, (e) —$OSO_2R^7$, (f) a halogen atom, (g) —O-$COR^7$, (h) —$NHCOR^8$, (i) $C_1$-$C_{20}$ alkoxy, (j) phenyl which may be substituted by one or more members selected from the group consisting of halogen, $C_1$-$C_{20}$ alkyl and nitro or (k) a saccharose residue, $R^2$ is a hydrogen atom or $C_1$-$C_{20}$ alkyl, $R^3$ is a hydrogen atom or a halogen atom, $R^4$ is (a) a hydrogen atom, (b) —$COR^9$, (c) silyl which may be substituted by one or more members selected from the group consisting of $C_1$-$C_{20}$ alkyl and phenyl or (d) $C_1$-$C_{20}$ alkyl which may be substituted by one or more members selected from the group consisting of $C_1$-$C_{20}$ alkoxy, phenyl and hydroxyl, one of $R^5$ and $R^6$ is (a) hydroxyl, (b) $C_1$-$C_{20}$ alkoxy which may be substituted by one or more members selected from the group consisting of $C_1$-$C_{20}$ alkoxy, phenyl and hydroxyl, (c) a saccharose residue, (d) $C_3$-$C_8$ cycloalkyloxy which may be substituted by one or more members selected from the group consisting of $C_2$-$C_{20}$ alkoxy, phenyl and hydroxyl or (e) —$OCOR^{10}$ and the other is a hydrogen atom or $C_1$-$C_{20}$ alkyl which may be substituted by one or more members selected from the group consisting of $C_1$-$C_{20}$ alkoxy, phenyl and hydroxyl, or $R^4$ and $R^5$ together form a single bond, while $R^6$ is a hydrogen atom or $C_1$-$C_{20}$ alkyl which may be substituted by one or more members selected from the group consisting of $C_1$-$C_{20}$ alkoxy, phenyl and hydroxyl, each of $R^7$, $R^9$ and $R^{10}$ is $C_1$-$C_{20}$ alkyl or phenyl which may be substituted by one or more members selected from the group consisting of halogen, $C_1$-$C_{20}$ alkyl and nitro, $R^8$ is (a) $C_1$-$C_{20}$ alkyl, (b) phenyl which may be substituted by one or more members selected from the group consisting of halogen, $C_1$-$C_{20}$ alkyl and nitro or (c) benzyloxy, X is (a) a hydrogen atom (b) $C_1$-$C_{20}$ alkyl which may be substituted by one or more members selected from the group consisting of halogen, hydroxyl, phenyl, $C_1$-$C_{20}$ alkyl-substituted, phenyl, pyridyl, furanyl, thienyl, acetoxy, vareloxy, azide and amino, (c) $C_2$-$C_{20}$ alkenyl which may be substituted by one or more members selected from the group consisting of halogen, hydroxyl, phenyl, $C_1$-$C_{20}$ alkyl-substituted phenyl, pyridyl, furanyl, thienyl, acetoxy, vareloxy, azide and amino, (d) $C_2$-$C_{20}$ alkynyl which may be substituted by one or more members selected from the group consisting of halogen, hydroxyl, phenyl, $C_1$-$C_{20}$ alkyl-substituted phenyl, pyridyl, furanyl, thienyl, acetoxy, vareloxy, azide and amino, (e) $C_3$-$C_8$ cycloalkyl which may be substituted by one or more members selected from the group consisting of halogen, hydroxyl, $C_1$-$C_{20}$ alkyl, acetoxy, vareloxy, nitro and amino, (f) phenyl which may be substituted by one or more members selected from the group consisting of halogen, hydroxyl, $C_1$-$C_{20}$ alkyl, acetoxy, vareloxy, nitro and amino, (g) pyridyl which may be substituted by one or more members selected from the group consisting of halogen, hydroxyl, $C_1$-$C_{20}$ alkyl, acetoxy, vareloxy, nitro and amino, (h) furanyl which may be substituted by one or more members selected from the group consisting of halogen, hydroxyl, $C_1$-$C_{20}$ alkyl, acetoxy, vareloxy, nitro and amino, (i) thienyl which may be substituted by one or more members selected from the group consisting of halogen, hydroxyl, $C_1$-$C_{20}$ alkyl, acetoxy, vareloxy, nitro and amino, (j) formyl, (k) —$COR^{11}$, (l) —$C(W^1)W^2R^{11}$ or (m) —$SO_2R^{11}$, wherein $R^{11}$ is (a) a chain hydrocarbon group which may be substituted by one or more members selected from the group consisting of halogen, $C_1$-$C_{18}$ alkoxy, halo $C_1$-$C_{18}$ alkoxy, $C_1$-$C_{18}$ alkylthio, $C_3$-$C_8$ cycloalkyl, $C_3$-$C_8$ cycloalkoxy, $C_5$-$C_8$ cycloalkenyl, $C_5$-$C_8$ cycloalkenyloxy, $C_1$-$C_{18}$ alkoxycarbonyl, $C_1$-$C_{18}$ carboxyl, $C_1$-$C_{18}$ alkyl carbonyl, $C_1$-$C_{18}$ alkylcarbonyloxy, aryl, aryloxy, arylthio, amino and $C_1$-$C_{18}$ alkyl-substituted amino, (b) a monocyclic hydrocarbon group which may be substituted by one or more members selected from the group consisting of halogen, $C_1$-$C_{18}$ alkyl, halo $C_1$-$C_{18}$ alkyl, $C_1$-$C_{18}$ alkoxy, halo $C_1$-$C_{18}$ alkoxy, $C_1$-$C_{18}$ alkylthio, $C_3$-$C_8$ cycloalkyl, $C_3$-$C_8$ cycloalkoxy, $C_5$-$C_8$ cycloalkenyl, $C_5$-$C_8$ cycloalkenyloxy, $C_1$-$C_{18}$ alkoxycarbonyl, $C_1$-$C_{18}$ alkylcarbonyl, $C_1$-$C_{18}$ alkylcarbonyloxy, aryl, aryloxy, arylthio, amino, $C_1$-$C_{18}$ alkyl-substituted amino, cyano, nitro and hydroxyl, (c) a polycyclic hydrocarbon group which may be substituted by one or more members selected from the group consisting of halogen, $C_1$-$C_{18}$ alkyl, halo $C_1$-$C_{18}$ alkyl, $C_1$-$C_{18}$ alkoxy, halo $C_1$-$C_{18}$ alkoxy, $C_1$-$C_{18}$ alkylthio, $C_3$-$C_8$ cycloalkyl, $C_3$-$C_8$ cycloalkoxy, $C_5$-$C_8$ cycloalkenyl, $C_5$-$C_8$ cycloalkenyloxy, $C_1$-$C_{18}$ alkoxycarbonyl, $C_1$-$C_{18}$ alkylcarbonyl, $C_1$-$C_{18}$ alkylcarbonyloxy, aryl, aryloxy, arylthio, amino, $C_1$-$C_{18}$ alkyl-substituted amino, cyano, nitro and hydroxyl, (d) a monocyclic heterocycle group which may be substituted by one or more members selected from the group consisting of halogen, $C_1$-$C_{18}$ alkyl, halo $C_1$-$C_{18}$ alkyl, $C_1$-$C_{18}$ alkoxy, halo $C_1$-$C_{18}$ alkoxy, $C_1$-$C_{18}$ alkylthio, $C_3$-$C_8$ cycloalkyl $C_3$-$C_8$ cycloalkoxy, $C_5$-$C_8$ cycloalkenyl, $C_5$-$C_8$ cycloalkenyloxy, $C_1$-$C_{18}$ alkoxycarbonyl, $C_1$-$C_{18}$ alkylcarbonyl, $C_1$-$C_{18}$ alkylcarbonyloxy, aryl, aryloxy, arylthio, amino, $C_1$-$C_{18}$ alkyl-substituted amino, cyano, nitro and hydroxyl, or (e) a polyacrylic heterocycle group which may be substituted by one or more members selected from the group consisting of halogen, $C_1$–$C_{18}$ alkyl, halo $C_1$–$C_{18}$ alkyl, $C_1$–$C_{18}$ alkoxy, halo $C_1$–$C_{18}$ alkoxy, $C_1$–$C_{18}$ alkylthio, $C_3$–$C_8$ cycloalkyl, $C_3$–$C_8$ cycloalkoxy, $C_5$–$C_8$ cycloalkenyl, $C_5$–$C_8$ cycloalkenyloxy, $C_1$–$C_{18}$ alkoxycarbonyl, $C_1$–$C_{18}$ alkylcarbonyl, $C_1$–$C_{18}$ alkylcarbonyloxy, aryl, aryloxy, arylthio, amino, $C_1$–$C_{18}$ alkyl-substituted amino, cyano, nitro and hydroxyl, wherein the heteroatom of said monocyclic and said polycyclic heterocycles is one or more heteroatoms selected from the group consisting of N, S and O, $W^1$ is an oxygen atom or a sulfur atom, $W^2$ is an oxygen atom, a sulfur atom or —NH—, Y is (a) a hydrogen atom, (b) $C_1$–$C_{20}$ alkyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino, (c) $C_2$–$C_{20}$ alkenyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino or (d) $C_2$–$C_{20}$ alkynyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino; and a pharmaceutically acceptable carrier.

2. The immuno-suppressive or anti-inflammatory pharmaceutical composition according to claim 1, wherein the enopyranose derivative of the formula (I) as defined in claim 1 or its salt is a stereoisomer of the following formula (I-1) or (I-2):

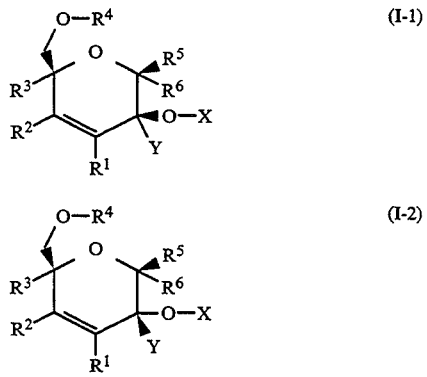

wherein $R^1$–$R^6$ are as defined in claim 1.

3. The immuno-suppressive or anti-inflammatory pharmaceutical composition according to claim 2, wherein the enopyranose derivative of the formula (I) or its salt is a compound represented by the formula (I-1) in which $R^1$ is (a) a hydrogen atom, (b) $C_1$–$C_{20}$ alkyl which may be substituted by one or more members selected from the group consisting of $C_1$–$C_{20}$ alkoxy, phenyl and hydroxyl, (c) $C_2$–$C_{20}$ alkenyl or (d) $C_2$–$C_{20}$ alkynyl, $R^2$ is a hydrogen atom or $C_1$–$C_{20}$ alkyl, $R^3$ and $R^6$ are respectively a hydrogen atom, and $R^4$ and $R^5$ together form a single bond.

4. The immuno-suppressive or anti-inflammatory pharmaceutical composition according to claim 1, wherein the enopyranose derivative of the formula (I) as defined in claim 1 or its salt is a compound or its salt selected from the group consisting of 1,6-anhydro-3,4-dideoxy-2-O-(2-furancarbonyl)-β-D-threo-hex-3-enopyranose, 1,6-anhydro-3,4-dideoxy-2-O-(2-furancarbonyl)-3-methyl-β-D-threo-hex-3-enopyranose, 1,6-anhydro-3,4-dideoxy-2-C-ethynyl-2-O-(2-furancarbonyl)-β-D-threo-hex-3-enopyranose, 1,6-anhydro-3,4-dideoxy-2-O-(2-furfuryl)-3-methyl-β-D-threo-hex-3-enopyranose, 1,6-anhydro-3,4-dideoxy-2-O-(2-furfuryl)-β-D-threo-hex-3-enopyranose and 1,6-anhydro-3,4-dideoxy-2-C-ethynyl-2-O-(2-furfuryl)-β-D-threo-hex-3-enopyranose.

5. A compound of the following formula (I-1) or (I-2):

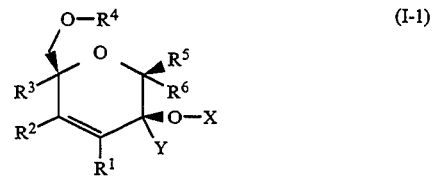

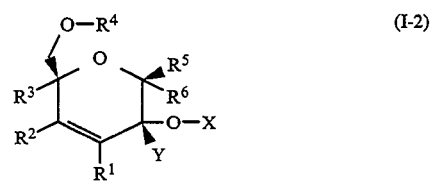

or its salt, wherein $R^1$ is (a) a hydrogen atom, (b) $C_1$–$C_{20}$ alkyl which may be substituted by one or more members selected from the group consisting of $C_1$–$C_{20}$ alkoxy, phenyl and hydroxyl, (c) $C_2$–$C_{20}$ alkenyl, (d) $C_2$–$C_{20}$ alkynyl, (e) —$OSO_2R^7$, (f) a halogen atom, (g) —$OCOR^7$, (h) —$NHCOR^8$, (i) $C_2$–$C_{20}$ alkoxy, (j) phenyl which may be substituted by one or more members selected from the group consisting of halogen, $C_1$–$C_{20}$ alkyl and nitro or (k) a saccharose residue, $R^2$ is a hydrogen atom or $C_1$–$C_{20}$ alkyl, $R^3$ is a hydrogen atom or a halogen atom, $R^4$ and $R^5$ together form a single bond, $R^6$ is a hydrogen atom or $C_1$–$C_{20}$ alkyl which may be substituted by one or more members selected from the group consisting of $C_1$–$C_{20}$ alkoxy, phenyl and hydroxyl, $R^7$ is $C_1$–$C_{20}$ alkyl or phenyl which may be substituted by one or more members selected from the group consisting of halogen, $C_1$–$C_{20}$ alkyl and nitro, $R^2$ is (a) $C_1$–$C_{20}$ alkyl, (b) phenyl which may be substituted by one or more members selected from the group consisting of halogen, $C_1$–$C_{20}$ alkyl and nitro or (c) benzyloxy, X is (a) a hydrogen atom (b) $C_1$–$C_{20}$ alkyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino, (c) $C_2$–$C_{20}$ alkenyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino, (d) $C_2$–$C_{20}$ alkynyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino, (e) $C_3$–$C_8$ cycloalkyl which may be substituted by one or more members selected from the group consisting of halogen, hydroxyl, $C_1$–$C_{20}$ alkyl, acetoxy, vareloxy, nitro and amino, (f) phenyl which may be substituted by one or mote members selected from the group consisting of halogen, hydroxyl, $C_1$–$C_{20}$ alkyl, acetoxy, vareloxy, nitro and amino, (g) pyridyl which may be substituted by one or more members selected from the group consisting of halogen, hydroxyl, $C_1$–$C_{20}$ alkyl, acetoxy, vareloxy, nitro and amino, (h) furanyl which may be substituted by one or more members selected from the group consisting of halogen, hydroxyl, $C_1$–$C_{20}$ alkyl, acetoxy, vareloxy, nitro and amino, (i) thienyl which may be substituted by one or more members selected from the group consisting of halogen, hydroxyl, $C_1$–$C_{20}$ alkyl, acetoxy, vareloxy, nitro and amino, (j) formyl, (k) —$COR^{11}$, (l) —$C(W^1)W^2R^{11}$or (m) —$SO_2R^{11}$, wherein $R^{11}$ is (a) a chain hydrocarbon group which may be substituted by one or more members selected from the group consisting of halogen, $C_1$–$C_{18}$ alkoxy, halo $C_1$–$C_{18}$ alkoxy, $C_1$–$C_{18}$ alkylthio, $C_3$–$C_8$ cycloalkyl, $C_3$–$C_8$ cycloalkoxy, $C_5$–$C_8$ cycloalkenyl, $C_5$–$C_8$ cycloalkenyloxy, $C_1$–$C_{18}$ alkoxycarbonyl, carboxyl, $C_1$–$C_{18}$ alkyl carbonyl, $C_1$–$C_{18}$ alkylcarbonyloxy, aryl, aryloxy, arylthio, amino and $C_1$–$C_{18}$ alkyl-substituted amino, (b) a monocyclic hydrocarbon group which may be substituted by one or more members selected from the group consisting of halogen, $C_1$–$C_{18}$ alkyl, halo, $C_1$–$C_{18}$ alkyl, $C_1$–$C_{18}$ alkoxy, halo $C_1$–$C_{18}$ alkoxy, $C_1$–$C_{18}$ alkylthio, $C_3$–$C_8$ cycloalkyl, $C_3$–$C_8$ cycloalkoxy, $C_5$–$C_8$ cycloalkenyl, $C_5$–$C_8$ cycloalkenyloxy, $C_1$–$C_{18}$ alkoxycarbonyl, $C_1$–$C_{18}$ alkylcarbonyl, $C_1$–$C_{18}$ alkylcarbonyloxy, aryl, aryloxy, arylthio, amino, $C_1$–$C_{18}$ alkyl-substituted amino, cyano, nitro and hydroxyl, (c) a polycyclic hydrocarbon group which may be substituted by one or more members selected from the group consisting of halogen, $C_1$–$C_{18}$ alkyl, halo $C_1$–$C_{18}$ alkyl, $C_1$–$C_{18}$ alkoxy, halo $C_1$–$C_{18}$ alkoxy $C_1$–$C_{18}$ alkylthio, $C_3$–$C_8$ cycloalkyl, $C_3$–$C_8$ cycloalkoxy, $C_5$–$C_8$ cycloalkenyl, $C_5$–$C_8$ cycloalkenyloxy, $C_1$–$C_{18}$ alkoxycarbonyl, $C_1$–$C_{18}$ alkylcarbonyl, $C_1$–$C_{18}$ alkylcarbonyloxy, aryl, aryloxy, arylthio, amino, $C_1$–$C_{18}$ alkyl-substituted amino, cyano, nitro and hydroxyl, (d) a monocyclic heterocycle group which may be substituted by one or more members selected from the group consisting of halogen, $C_1$–$C_{18}$ alkyl, halo $C_1$–$C_{18}$ alkyl, $C_1$–$C_{18}$ alkoxy, halo $C_1$–$C_{18}$ alkoxy, $C_1$–$C_{18}$ alkylthio, $C_3$–$C_8$ cycloalkyl, $C_3$–$C_8$ cycloalkoxy, $C_5$–$C_8$ cycloalkenyl, $C_5$–$C_8$ cycloalkenyloxy, $C_1$–$C_{18}$ alkoxycarbonyl, $C_1$–$C_{18}$ alkylcarbonyl, $C_1$–$C_{18}$ alkylcarbonyloxy, aryl, aryloxy, arylthio, amino, $C_1$–$C_{18}$ alkyl-substituted amino, cyano, nitro and hydroxyl, or (e) a polycyclic heterocycle group which may be substituted by one or more members selected from the group consisting of halogen, $C_1$–$C_{18}$ alkyl, halo $C_1$–$C_{18}$ alkyl, $C_1$–$C_{18}$ alkoxy, halo $C_1$–$C_{18}$ alkoxy, $C_1$–$C_{18}$ alkylthio, $C_3$–$C_8$ cycloalkyl, $C_3$–$C_8$ cycloalkoxy, $C_5$–$C_8$ cycloalkenyl, $C_5$–$C_8$ cycloalkenyloxy, $C_1$–$C_{18}$ alkoxycarbonyl, $C_1$–$C_{18}$ alkylcarbonyl, $C_1$–$C_{18}$ alkylcarbonyloxy, aryl, aryloxy, arylthio, amino, $C_1$–$C_{18}$ alkyl-substituted amino, cyano, nitro and hydroxyl, wherein the heteroatom of said monocyclic and said polycyclic heterocycles is one or more heteroatoms selected from the group consisting of N, S and O, $W^1$ is an oxygen atom or a sulfur atom, $W^2$ is an oxygen atom, a sulfur atom or —NH—, Y is (a) a hydrogen atom, (b) $C_1$–$C_{20}$ alkyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino, (c) $C_2$–$C_{20}$ alkenyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino or (d) $C_2$–$C_{20}$ alkynyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino, provided that the following cases are excluded:

(1) a case where in the formula (I-1) each of $R^1$, $R^2$, $R^3$, $R^6$ and X is a hydrogen atom, and Y is a hydrogen atom or alkyl which may be substituted, (2) a case where in the formula (I-1), each of $R^1$, $R^2$, $R^3$, $R^6$ and Y is a hydrogen atom, X is acetyl, 3,5-dinitrobenzoyl or p-toluenesulfonyl, (3) a case where in the formula (I-1), each of $R^1$, $R^2$, $R^3$ and Y is a hydrogen atom, $R^6$ is alkyl which may be substituted, and X is a hydrogen atom or acetyl, (4) a case where in the formula (I-2), each of $R^1$, $R^2$, $R^3$, $R^6$ and X is a hydrogen atom, and Y is methyl, (5) a case where in the formula (I-2), each of $R^1$, $R^2$, $R^3$, $R^6$ and Y is a hydrogen atom, and X is a hydrogen atom, methyl, benzyl, formyl, acetyl, benzoyl, 4-chlorobenzoyl, 3,5-dichlorobenzoyl, 4-nitrobenzoyl, 3,5-dinitrobenzoyl, 4-methoxybenzoyl, 3,5-dimethoxybenzoyl, methylsulfonyl or p-toluenesulfonyl, and (6) a case where in the formula (I-2), $R^1$ is p-toluenesulfonyloxy, each of $R^2$, $R^3$, $R^6$ and Y is a hydrogen atom, and X is a hydrogen atom, acetyl or p-toluenesulfonyl.

6. The compound or its salt according to claim 5, wherein the compound of the formula (I-1) or (I-2) or its salt is a compound represented by the formula (I-1) in which $R^1$ is (a) a hydrogen atom, (b) $C_1$–$C_{20}$ alkyl which may be substituted by one or more members selected from the group consisting of $C_1$–$C_{20}$ alkoxy, phenyl and hydroxyl, (c) $C_2$–$C_{20}$ alkenyl or (d) $C_2$–$C_{20}$ alkynyl, $R^2$ is a hydrogen atom or $C_1$–$C_{20}$ alkyl, $R^3$ and $R^6$ are respectively a hydrogen atom, $R^4$ and $R^5$ together form a single bond.

7. The compound or its salt according to claim 5, wherein the compound of the formula (I-1) or (I-2) or its salt is a compound represented by the formula (I-1) in which $R^1$ is (a) a hydrogen atom, (b) $C_1$–$C_{20}$ alkyl which may be substituted by one or more members selected from the group consisting of $C_1$–$C_{20}$ alkoxy, phenyl and hydroxyl, (c) $C_2$–$C_{20}$ alkenyl or (d) $C_2$–$C_{20}$ alkynyl, $R^2$ is a hydrogen atom or $C_1$–$C_{20}$ alkyl, $R^3$ and $R^6$ are respectively a hydrogen atom, X is (a) $C_1$–$C_{20}$ alkyl which may be substituted by one or more members selected from the group consisting of halogen, hydroxyl, phenyl, $C_1$–$C_{20}$ alkyl-substituted phenyl, pyridyl, furanyl, thienyl, acetoxy, vareloxy, azide and amino or (b) —$COR^{11}$.

8. The compound or its salt according to claim 7, wherein X is (a) furfuryl or (b) —$COR^{11}$ in which $R^{11}$ is furanyl which may be substituted by one or more members selected from the group consisting of halogen, hydroxyl, $C_1$–$C_{20}$ alkyl, acetoxy, vareloxy, nitro and amino.

9. A compound or its salt according to claim 7, wherein the compound as defined in claim 7 or its salt is a compound or its salt selected from the group consisting 1,6-anhydro-3,4-dideoxy-2-O-(2-furancarbonyl)-β-D-threo-hex- 3-enopyranose, 1,6-anhydro-3,4-dideoxy-2-O-(2-furancarbonyl)-3-methyl-β-D-threo-hex-3-enopyranose, 1,6-anhydro-3,4-dideoxy-2-C-ethynyl-2-O-(2-furancarbonyl)-β-D-threo-hex-3-enopyranose, 1,6-anhydro-3,4-dideoxy-2-O-(2-furfuryl)-β-D-threo-hex-3-enopyranose, 1,6-anhydro-3,4-dideoxy-2-O-(2-furfuryl)-3-methyl-β-D-threo-hex-3-enopyranose and 1,6-anhydro-3,4-dideoxy-2-C-ethynyl-2-O-(2-furfuryl)-β-D-threo-hex-3-enopyranose.

10. An immuno-suppressive agent or an anti-inflammatory agent according to claim 1, wherein the enopyranose derivative of the formula (I) as defined in claim 1 or its salt is 1,6-anhydro-3,4-dideoxy-4-methyl-β-D-threo-hex-3-enopyranose.

* * * * *